United States Patent [19]
Cantello

[11] Patent Number: 4,629,737
[45] Date of Patent: Dec. 16, 1986

[54] SECONDARY AMINES AND USE IN PHARMACEUTICAL COMPOSITIONS

[75] Inventor: Barrie C. C. Cantello, Redhill, England

[73] Assignee: Beecham Group p.l.c., England

[21] Appl. No.: 513,869

[22] Filed: Jul. 14, 1983

[30] Foreign Application Priority Data

Jul. 16, 1982 [GB] United Kingdom ................ 8220645
Oct. 7, 1982 [GB] United Kingdom ................ 8228753
Dec. 15, 1982 [GB] United Kingdom ................ 8235672

[51] Int. Cl.[4] ................ C07C 101/16; C07C 101/447; A61K 31/215; A61K 31/195

[52] U.S. Cl. ...................... 514/564; 514/562; 514/567; 514/618; 514/619; 514/620; 560/17; 560/42; 560/43; 562/431; 562/457; 562/442; 562/452; 564/162; 564/165; 564/167

[58] Field of Search ............ 560/45, 42, 43, 17; 562/442, 451, 431, 457, 452; 564/355, 165, 162, 167; 514/562, 564, 567, 618, 619, 620, 539

[56] References Cited

U.S. PATENT DOCUMENTS

| | | | |
|---|---|---|---|
| 4,338,333 | 7/1982 | Ainsworth et al. | 562/451 X |
| 4,385,066 | 5/1983 | Ainsworth et al. | 564/165 X |
| 4,396,627 | 8/1983 | Ainsworth et al. | 562/451 X |
| 4,478,849 | 10/1984 | Ainsworth et al. | 560/42 X |

FOREIGN PATENT DOCUMENTS

| | | | |
|---|---|---|---|
| 28105 | 5/1981 | European Pat. Off. | |
| 0040000 | 11/1981 | European Pat. Off. | 560/45 |
| 52963 | 6/1982 | European Pat. Off. | |
| 1340457 | 12/1973 | United Kingdom | |

OTHER PUBLICATIONS

Burger's Medicinal Chemistry, 4th Ed., Part 1 (1980), pp. 167-168.
T. E. Gram, Concepts in Biochemical Pharmacology, Pt. 2, B. B. Brodie and J. R. Gillette, Eds., Springer-Verlage, Berlin (1971), p. 334.
A. Nilsson and B. C. Johnson, Arch. Biochem. Biophys., 101, 494 (1963).
W. J. George and T. R. Tephyl, Mol. Pharmacol., 4, 502, (1968).

*Primary Examiner*—Bernard Helfin
*Attorney, Agent, or Firm*—Jacobs & Jacobs

[57] ABSTRACT

A compound of formula (I):

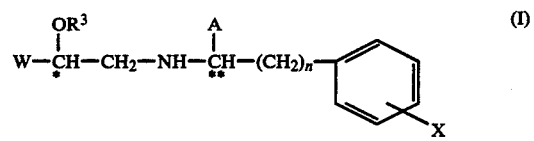

or a pharmaceutically acceptable salt, ester or amide thereof, in which:

W is an optionally substituted phenyl group of the formula

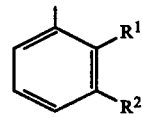

wherein $R^1$ is hydrogen or fluorine,
$R^2$ is hydrogen, $C_{1-6}$ alkyl, halogen or trifluoromethyl; or W is a phenoxymethyl or benzofuran-2-yl group;
$R^3$ is $C_{1-12}$ alkyl or phenyl $C_{1-6}$ alkyl;
A is hydrogen or methyl,
X is carboxy, —Z—$CO_2$H, —Z—OH, T—Z—$CO_2$H, —Z—$NR^4R^5$, —T—Y—OM, —T—Y—$NR^4R^5$, or —T—$R^6$, in the para- or meta-position with respect to the —$(CH_2)_n$ group,
wherein
$R^4$ and $R^5$ are each hydrogen or $C_{1-6}$ alkyl,
$R^6$ is $C_{1-6}$ alkyl,
T is O, S, —NH or —N—$R^7$, in which $R^7$ is $C_{1-6}$ alkyl
Z is $C_{1-10}$ straight or branched alkylene optionally containing a carbon-carbon double bond;
Y is $C_{2-10}$ straight or branched alkylene, provided that the hetero atoms in —T—Y—OM and —T—Y—$NR^4R^5$ are separated by at least two carbon atoms, M is hydrogen, $C_{1-6}$ alkyl or phenyl, and n is 1 or 2, is useful for obesity or hyperglycaemia.

27 Claims, No Drawings

SECONDARY AMINES AND USE IN PHARMACEUTICAL COMPOSITIONS

The present invention relates to derivatives of 2-aminoethyl ether which have anti-hyperglycaemic and/or anti-obesity and/or anti-inflammatory and/or platelet aggregation inhibition activity, to processes for their production and to their use in medicine.

U.K. Patent Specification No. 1,340,457 discloses compounds of the general formula:

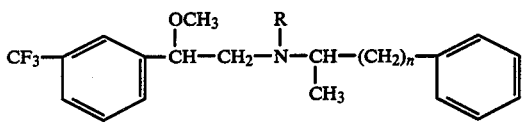

in which R represents hydrogen or $C_{1-3}$ alkyl, and n is 0 or 1. These compounds are stated to be anorectic agents.

It has now been discovered that a class of novel 2-aminoethyl ether derivatives have anti-hyperglycaemic and/or anti-obesity and/or anti-inflammatory and/or platelet aggregation inhibition activity. These activities are coupled with low cardiac stimulant activity.

According to the present invention there is provided a compound of formula (I):

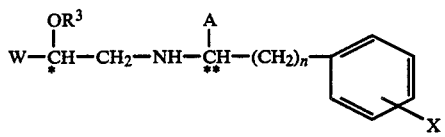

or a pharmaceutically acceptable salt, ester or amide thereof, in which:

W is an optionally substituted phenyl group of the formula

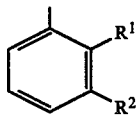

wherein $R^1$ is hydrogen or fluorine,
$R^2$ is hydrogen, $C_{1-6}$ alkyl, halogen or trifluoromethyl;
or W is a phenoxymethyl or benzofuran-2-yl group;
$R^3$ is $C_{1-12}$ alkyl or phenyl $C_{1-6}$ alkyl;
A is hydrogen or methyl,
X is carboxy, $-Z-CO_2H$, $-Z-OH$, $T-Z-CO_2H$, $-Z-NR^4R^5$, $-T-Y-OM$, $-T-Y-NR^4R^5$, or $-T-R^6$, in the para- or meta-position with respect to the $-(CH_2)_n$ group,
wherein
$R^4$ and $R^5$ are each hydrogen or $C_{1-6}$ alkyl,
$R^6$ is $C_{1-6}$ alkyl,
T is O, S, $-NH$ or $-N-R^7$, in which $R^7$ is $C_{1-6}$ alkyl
Z is $C_{1-10}$ straight or branched alkylene optionally containing a carbon-carbon double bond;
Y is $C_{2-10}$ straight or branched alkylene, provided that the hetero atoms in $-T-Y-OM$ and $-T-Y-NR^4R^5$ are separated by at least two carbon atoms, M is hydrogen, $C_{1-6}$ alkyl or phenyl and n is 1 or 2.

$R^3$ may be a straight or branched chain alkyl group, and is preferably $C_{1-6}$ alkyl, more preferably methyl. When $R^3$ is phenyl $C_{1-6}$ alkyl, it is preferably benzyl. Preferably $R^2$ is chlorine or trifluoromethyl.

Preferably, A is methyl;
Preferably Z is $-CH_2-$ and preferably Y is $-(CH_2)_2-$.

$R^4$ and $R^5$ may simultaneously both be hydrogen or $C_{1-6}$ alkyl although it is preferred that one is hydrogen and the other is alkyl.

T is preferably oxygen.

The preferred position of the X group is the para position.

Pharmaceutically acceptable salts of compounds of formula (I) include acid addition salts formed with a pharmaceutically acceptable acid such as hydrochloric acid, hydrobromic acid, orthophosphoric acid, sulphuric acid, methanesulphonic acid, toluenesulphonic acid, acetic acid, propionic acid, lactic acid, citric acid, fumaric acid, malic acid, succinic acid, salicylic acid or acetylsalicylic acid.

Preferred esters of the compounds of formula (I) are $C_{1-6}$ alkyl esters of the compounds wherein X is carboxy, $-Z-CO_2H$ or $-T-Z-CO_2H$. Particularly preferred esters are the methyl and ethyl esters.

Preferred amides of the compounds of formula (I) are those wherein the carboxy group is modified to a group of the formula $-CONR^4R^5$, $-Z-CO_2H$ is modified to $-Z-CONR^4R^5$ and $-T-Z-CO_2H$ is modified to $-T-Z-CONR^4R^5$, wherein T, Z, $R^4$ and $R^5$ are as defined in formula (I).

When A is methyl, the compounds of formula (I) have two asymmetric carbon atoms, marked with single and double asterisks in the formula. These compounds may, therefore, exist in four stereoisomeric forms. The present invention encompasses all stereoisomers of the compounds of formula (I) whether free from other stereoisomers or admixed with other stereoisomers in any proportion and thus includes, for instance, racemic mixtures of enantiomers.

In addition, when Z contains a carbon-carbon double bond, each stereoisomer can exist as two geometric isomers having the (E) or (Z) absolute configuration. The invention encompasses both geometric isomers whether as individual isomers or in admixture with each other in any proportion.

Preferably the carbon atom marked with a single asterisk has the R configuration.

The most potent compounds of formula (I) are those wherein both asymmetric carbon atoms are in the R configuration.

The absolute configuration of any compound of formula (I) may be determined by conventional X-ray crystallographic techniques.

The present invention also provides a process for producing a compound of formula (I) or a pharmaceutically acceptable salt, ester or amide thereof, which comprises reducing an oxo-group or a double bond and/or a moiety reducible to a group X of a compound of formula (II), or an ester or amide thereof:

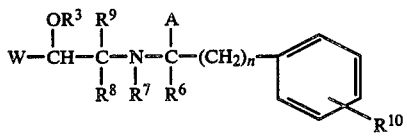 (II)

wherein
- $R^3$, W, n and A are as defined in formula (I),
- $R^6$ is hydrogen or together with $R^7$ forms a bond;
- $R^7$ is hydrogen or together with $R^6$, or $R^8$ forms a bond;
- $R^8$ is hydrogen or together with $R^9$ forms an oxo-group or together with $R^7$ forms a bond;
- $R^9$ is hydrogen or together with $R^8$ forms an oxo-group, and
- $R^{10}$ is X or a moiety reducible to X as defined in relation to formula I,
  provided $R^6$ to $R^9$ are not simultaneously all hydrogen when $R^{10}$ is X, and optionally thereafter forming a salt of the compound of formula (I) so formed, and/or converting the compound of formula (I) so formed into a further compound of formula (I).

The salts of the compounds of formula (I) may be produced by treating the compounds of formula (I) with the appropriate acid or base.

The reduction of the compounds of formula (II) may be effected by conventional chemical or catalytic methods, such as chemical reduction using lithium aluminium hydride, sodium cyanoborohydride or sodium borohydride or borane methylsulphide or by catalytic hydrogenation using catalysts such as palladium on charcoal, or platinum, for instance, as platinum oxide.

Reduction by sodium borohydride is conveniently effected in a lower alkanolic solvent such as methanol or ethanol. The reaction is generally carried out at from 0°-20° C.

Reduction by lithium aluminium hydride is conveniently effected in a dry, ether solvent such as diethyl ether or tetrahydrofuran at ambient or elevated temperature.

Catalytic reduction is conveniently effected in a conventional hydrogenation solvent such as a lower alkanol, for instance ethanol. The hydrogenation is generally carried out under hydrogen gas at about 1 atmosphere pressure to about 10 atmospheres pressure and at ambient or elevated temperature.

Suitable groups for $R^{10}$ include cyanoalkyl, cyanoalkoxy, carboxamido or amino-carbonylalkoxy groups which may be reduced, for instance, catalytically or using lithium aluminium hydride or borane methylsulphide, to provide the corresponding aminoalkoxy group $-O-Y-NR^4R^5$.

Conventional processes may be used to convert compounds of formula (I) into further compounds of formula (I). For example, a compound of formula (I) wherein $R^4$ or $R^5$ is hydrogen may be derivatised to produce further compounds of formula (I).

Compounds of formula (I) may be separated into diastereoisomeric pairs of enantiomers by, for example, fractional crystallisation from a suitable solvent such as methanol or ethyl acetate or a mixture thereof. The pair of enantiomers thus obtained may be separated into individual stereoisomers by conventional means such as by the use of an optically active acid as a resolving agent.

Suitable optically active acids which may be used as resolving agents are described in 'Topics in Stereochemistry', Vol. 6, Wiley Interscience, 1971, Allinger, N. L. and Eliel, W. L. Eds.

Alternatively any enantiomer of a compound of formula (I) may be obtained by stereospecific synthesis using an optically pure starting material of known configuration.

Compounds of formula (II) may be prepared by treating a compound of formula (III):

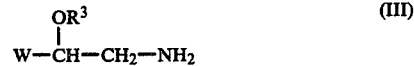 (III)

wherein W and $R^3$ are as defined in relation to formula (I); with a compound of formula (IV), or an ester or amide thereof:

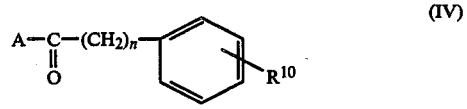 (IV)

wherein A and n are as defined in formula (I) and $R^{10}$ is as defined in formula (II), or with a compound of formula (V), or an ester or amide thereof:

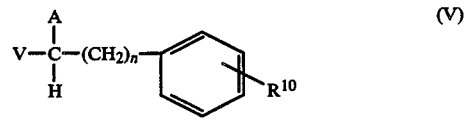 (V)

wherein A, and n are as defined in formula (I), $R^{10}$ is as defined in formula (II) and V is a good leaving group, suitably halogen or tosyloxy.

When $R^{10}$ in the compound of formula (V) is X, the reaction between compounds of formulae (III) and (V) provides a compound of formula (I) directly.

The reaction of a compound of formula (III) with a compound of formula (IV) is conveniently effected under conditions which result in the removal of water formed during the reaction. A particularly suitable method is to perform the reaction in a solvent, such as benzene, under reflux and azeotropically to remove the water using a Dean and Stark trap.

The reaction of a compound of formula (III) with a compound of formula (V) is conveniently effected in a solvent such as dimethylsulphoxide at elevated temperature, preferably about 50° C. for about two to three days.

Compounds of formula (II) may also be prepared by reacting a compound of formula (VI), or an ester or amide thereof:

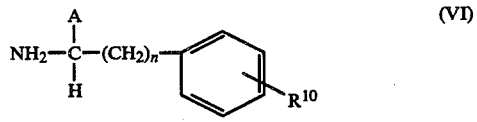 (VI)

wherein A, and n are as defined in formula (I), and $R^{10}$ is as defined in formula (II), with a compound of formula (VII):

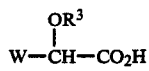

(VII)

wherein W and $R^3$ are as defined in formula (I).

The reaction between compounds of formulae (VI) and (VII) is conveniently conducted under standard peptide formation reaction conditions, for example, in the presence of dicyclohexylcarbodiimide, 1-hydroxybenztriazole and dimethylformamide.

By using single enantiomers of the compounds of formulae (VI) and (VII) a stereospecific synthesis of a compound of formula (II) is achieved. The compound of formula (II) may then be reduced to a compound of formula (I) without altering the configuration of the two asymmetric carbon atoms. Thus, for example, a compound of formula (VI) with the R-absolute configuration and a compound of formula (VII) with the R-absolute configuration would afford a compound of formula (II) and by subsequent reduction afford a compound of formula (I) with an R,R-absolute configuration.

The compounds of formulae (III), (IV), (V), (VI) and (VII) are either known compounds or can be prepared from known compounds by literature methods.

It is often convenient to prepare the compound of formula (II) and reduce it to the desired compound of formula (I) without isolation of the compound of formula (II).

A compound of formula (I) or a pharmaceutically acceptable salt, ester or amide thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt, ester or amide thereof with a pharmaceutically acceptable carrier therefor.

As used herein the terms 'pharmaceutical composition' and 'pharmaceutically acceptable' embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed-unit dosage forms, such as powders presented in sachets, may also be used.

In accordance with conventional pharmaceutical practice the carrier may comprise a diluent, binder, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg of the drug, more usually 0.1 to 250 mg and favourably 0.1 to 100 mg.

The present invention further provides a method for treating hyperglycaemia in human or non-human animals which method comprises administering an effective, non-toxic amount of a compound of formula (I) or a pharmaceutically acceptable salt, ester or amide thereof to a hyperglycaemic animal.

Conveniently, the drug may be administered as a pharmaceutical composition as hereinbefore defined, and this forms a particular aspect of the present invention.

In treating hyperglycaemic humans the drug may be taken in doses, such as those described above, one to six times a day in a manner such that the total daily dose for a 70 kg adult will generally be about 0.1 to 3000 mg, and more usually about 1 to 500 mg.

The present invention further provides a method for treating obesity in human or non-human animals, which method comprises administering an effective, non-toxic amount of a compound of formula (I) or a pharmaceutically acceptable salt, ester or amide thereof to an obese animal.

The dose for obese humans is similar to that for hyperglycaemic humans.

In treating obese domestic animals, especially dogs, the drug may be administered by mouth, usually once or twice a day and at about 0.025 mg/kg to 25 mg/kg, for example 0.1 mg/kg to 20 mg/kg.

The present invention also provides a method for the treatment or prophylaxis of inflammation in human or non-human animals, which comprises topically administering an effective non-toxic amount of a compound of formula (I) or a pharmaceutically acceptable salt, ester or amide thereof to an animal suffering inflammation.

The present invention further provides a method of inhibiting platelet aggregation in humans, which comprises administering to the sufferer an effective non-toxic amount of a compound of formula (I) or a pharmaceutically acceptable salt, ester or amide thereof.

The invention will now be illustrated with reference to the following Examples, which are not intended to limit the scope in any way. Examples 1 to 60 are examples of compounds of the invention, and Examples X1 to X27 are examples of intermediates.

EXAMPLE 1

N-[2-(4-Carbomethoxymethoxyphenyl)-1-methylethyl]-2-methoxy-2-(3-chlorophenyl)ethanamine hydrochloride 1-(4-carbomethoxymethoxyphenyl)propan-2-one (2.80 g) and 2-methoxy-2-(3-chlorophenyl)ethanamine (2.58 g) in dry toluene (200 ml) were boiled under reflux for 2 hours in an apparatus incorporating a water trap. The solution was cooled and the solvent removed under reduced pressure. The residue dissolved in methanol (100 ml) was hydrogenated in the presence of platinum (from platinum oxide, 50 mg) until hydrogen uptake ceased. The solution was filtered through diatomaceous earth, and the solvent removed under reduced pressure. Chromatography of the residue on silica-gel in 3% methanol-dichloromethane gave an oil. Treatment of this oil with an ethereal solution of hydrogen chloride gave N-[2-(4-carbomethoxymethoxyphenyl)-1-methylethyl]-2-methoxy-2-(3-chlorophenyl)ethanamine hydrochloride, mp 148°–50° C. (ethyl acetate), as an 85:15 mixture of diastereoisomers.

$^1$H nmr (DMSO-$d_6$)

1.05 (3H, d); 3.5–2.5 (8H, complex); 3.7 (3H, s), 4.8 (3H, complex); 6.9 (2H, d); 7.15 (2H, d); 7.45 (4H, complex); 8.5–10 (2H, broad signals, exchange with $D_2O$).

The mother liquors from the above crystallisation were evaporated to dryness and the residual oil reconverted to its free base to give an oil which was subsequently used in Example 9.

EXAMPLE 2

N-[2-(4-Carbomethoxymethoxyphenyl)-1-methylethyl]-2-methoxy-2-(3-trifluoromethylphenyl)ethanamine hydrochloride 1-(4-Carbomethoxymethoxyphenyl)propan-2-one (5.92 g) and 2-methoxy-2-(3-trifluoromethylphenyl)ethanamine (5.84 g) were condensed and subsequently reduced by an analogous procedure to that described in Example 1. Chromatography on silica-gel in 2-4% methanoldichloromethane gave an oil, which on treatment with an ethereal solution of hydrogen chloride gave N-[2-(4-carbomethoxymethoxyphenyl)-1-methylethyl]-2-methoxy-2-(3-trifluoromethylphenyl)ethanamine hydrochloride, mp 135°-9° C. (methanol-ethyl acetate-diethyl ether-hexane), as a 89:11 mixture of diastereoisomers.

$^1$H nmr $\delta$(DMSO-d$_6$)

1.0 (3H, d); 2.4-3.5 (8H, complex); 3.65 (3H, s); 4.8 (2H, s); 4.9 (1H, t); 6.9 (2H, d); 7.2 (2H, d); 7.8 (4H, s); 8.6-10.3 (2H, broad signals, exchange with D$_2$O).

The mother liquors from the above crystallisation were evaporated to dryness and the residual oil reconverted to its free base to give an oil which was subsequently used in Example 7.

EXAMPLE 3

N-[2-(4-Carbomethoxymethoxyphenyl)-1-methylethyl]-2-ethoxy-2-(3-chlorophenyl)ethanamine hydrochloride 1-(4-carbomethoxymethoxypheny)propan-2-one (5.04 g) and 2-ethoxy-2-(3-chlorophenyl)ethanamine (4.53 g) were condensed and subsequently reduced by an analogous procedure to that described in Example 1. Chromatography on silica-gel in 2-4% methanol-dichloromethane gave an oil, which on treatment with an ethereal solution of hydrogen chloride gave N-[2-(4-carbomethoxymethoxyphenyl)-1-methylethyl]-2-ethoxy-2-(3-chlorophenyl)ethanamine hydrochloride, mp 100°-101° C. (methanol-ethyl acetate-diethyl ether), as a 59:41 mixture of diastereoisomers.

$^1$H nmr $\delta$(DMSO-d$_6$)

1.0-1.3 (6H, complex); 2.5-3.6 (7H, complex); 3.7 (3H, s); 4.7 (2H, s); 4.95 (1H, t); 6.9 (2H, d); 7.2 (2H, d); 7.5 (4H, complex); 8.6-10 (2H, broad signals, exchange with D$_2$O).

EXAMPLE 4

N-[2-(4-Methylaminocarbonylmethoxyphenyl)-1-methylethyl]-2-methoxy-2-(3-chlorophenyl)ethanamine hydrochloride To a solution of N-[2-(4-carbomethoxymethoxyphenyl)-1-methylethyl]-2-methoxy-2-(3-chlorophenyl)ethanamine hydrochloride (0.63 g, diastereoisomeric ratio 92:8) in methanol was added 5 ml of a 30% aqueous solution of methylamine. This mixture was boiled under reflux for 6 hours during which time 3 further 5 ml portions of the methylamine solution were added. The solution was cooled to room temperature, a further 5 ml of methylamine solution added and the reaction mixture allowed to stand at room temperature overnight. After diluting with saturated sodium chloride solution the mixture was extracted with dichloromethane, washed with saturated sodium chloride solution, dried (magnesium sulphate), filtered and evaporated to give an oil which was converted to its hydrochloride salt by addition of ethereal hydrogen chloride. Recrystallisation from methanol-ethyl acetate gave the title compound, mp 217°-9° C., as single diastereoisomer.

$^1$H nmr $\delta$(DMSO-d$_6$)

1.1 (3H, d); 2.65 (4H, d, on m); 3.0-3.5 (7H, complex); 4.4 (2H, s); 4.8 (1H, m); 6.8-7.3 (4H, dd); 7.3-7.6 (4H, complex); 8.1 (1H, exchanges with D$_2$O); 8.5-9.8 (2H, broad, exchange with D$_2$O).

EXAMPLE 5

N-[2-(4-Carbomethoxyphenyl)-1-methylethyl]-2-methoxy-2-(3-chlorophenyl)ethanamine hydrochloride 1-(4-Carbomethoxyphenyl)-propan-2-one (2.35 g) and 2-methoxy-2-(3-chlorophenyl)ethanamine (2.27 g) in dry toluene (100 ml) were boiled under reflux for 1 hour in an apparatus incorporating a water-trap. The solution was cooled and the solvent removed under reduced pressure. The residue dissolved in methanol (100 ml) was hydrogenated in the presence of platinum (from platinum oxide, 50 mg) until hydrogen uptake ceased. The solution was filtered through diatomaceous earth and the solvent removed under reduced pressure. Chromatography of the residue on silica-gel in 0-4% methanol-dichloromethane gave an oil, which on treatment with an ethereal solution of hydrogen chloride gave N-[2-(4-carbomethoxyphenyl)-1-methylethyl]-2-methoxy-2-(3-chlorophenyl)ethanamine hydrochloride, mp 180°-183° C. (methanol-ethyl acetate), as an 88:12 mixture of diastereoisomers.

$^1$H nmr $\delta$(DMSO-d$_6$)

1.15 (3H, d); 2.7-3.7 (8H, complex); 3.8 (3H, s); 4.8 (1H, complex); 7.3-7.6 (6H, complex); 7.9 (2H, d); 8.8-10.5 (2H, broad, exchange on addition of D$_2$O).

EXAMPLE 6

N-[2-(4-(2-Methylaminoethoxy)phenyl)-1-methylethyl]-2-methoxy-2-(3-chlorophenyl)ethanamine dihydrochloride To a stirred solution of N-[2-(4-methylaminocarbonylmethoxyphenyl)-1-methylethyl]-2-methoxy-2-(3-chlorophenyl)ethanamine (0.50 g; 85:15 mixture of diastereoisomers) in dry tetrahydrofuran (20 ml) was added borane-methyl sulphide complex (2 ml), under nitrogen. The solution was boiled under reflux for 3 hours, and after cooling to room temperature, methanol (6 ml) was added. This solution was allowed to stand overnight at room temperature, boiled under reflux for 1 hour, cooled, and hydrogen chloride gas passed through for 10 minutes. After dilution with diethyl ether, cooling to 0° C. and filtering, N-[2-(4-(2-methylaminoethoxy)phenyl)-1-methylethyl]-2-methoxy-2-(3-chlorophenyl)ethanamine dihydrochloride, mp 270°-273° C. (methanol-ethyl acetate), was obtained as a single diastereoisomer.

$^1$H nmr $\delta$(DMSO-d$_6$+methanol-d$_4$)

1.15 (3H, d), 2.65-3.5 (13H, complex), 3.8-4.3 (6H, complex, 4H exchange on addition of D$_2$O), 4.7 (1H, q), 6.9 (2H, d), 7.2 (2H, d), 7.4 (4H, complex).

The synthesis of a sample enriched in the other diastereoisomer is described in Example 9.

EXAMPLE 7

N-[2-(4-Methylaminocarbonylmethoxyphenyl)-1-methylethyl]-2-methoxy-2-(3-trifluoromethylphenyl)ethanamine hydrochloride The title compound, mp 193°–5° C. (methanol-ethyl acetate) was obtained as a 67:33 mixture of diastereoisomers from N-[2-(4-carbomethoxymethoxyphenyl)-1-methylethyl]-2-methoxy-2-(3-trifluoromethylphenyl)ethanamine (obtained from the mother liquors of Example 2) by an analogous procedure to that described in Example 4.

$^1$H nmr δ(DMSO-d$_6$)

1.1 (3H, d), 2.6 (4H, d on m), 3.1–3.4 (7H, complex), 4.4 (2H, s), 4.95 (1H, m), 6.8–7.3 (4H, dd), 7.75 (4H, complex), 8.1 (1H, exchanges with D$_2$O), 8.9 (1H, exchanges with D$_2$O), 10.0 (1H, exchanges with D$_2$O).

EXAMPLE 8

N-[2-(3-Carbomethoxymethoxyphenyl)-1-methylethyl]-2-methoxy-2-(3-chlorophenyl)ethanamine hydrochloride The title compound, mp 82°–7° C. (ethyl acetate), was obtained, as a 90:10 mixture of diastereoisomers, from 2-methoxy-2-(3-chlorophenyl)ethanamine and 1-(3-carbomethxymethoxyphenyl)propan-2-one by an analogous procedure to that described in Example 1.

$^1$H nmr δ(DMSO-d$_6$)

1.15 (3H, d), 2.6 (1H, m), 3.0–3.45 (7H, complex), 3.7 (3H, s), 4.7–4.9 (3H, s on m), 6.7–7.6 (8H, complex), 8.5–10.0 (2H, exchange with D$_2$O).

EXAMPLE 9

N-[2-(4-Methylaminoethoxy)phenyl)-1-methylethyl]-2-methoxy-2-(3-chlorophenyl)ethanamine dihydrochloride The title compound, mp 256°–8° C. (methanol-ethyl acetate) was obtained, as a 22:78 mixture of diastereoisomers, from N-[2-(4-carbomethoxymethoxyphenyl)-1-methylethyl]-2-methoxy-2-(3-chlorophenyl)ethanamine (obtained from the mother liquors of Example 1) by reaction with methylamine and subsequent reduction with borane-methyl sulphide by analogous procedures to that described in Examples 4 and 6 respectively.

$^1$H nmr δ(DMSO-d$_6$)

1.15 (3H, d), 2.65–3.5 (13H, complex), 3.8–4.3 (6H, complex, 4H exchange on addition of D$_2$O), 4.7 (1H, q), 6.9 (2H, d), 7.2 (2H, d), 7.4 (4H, complex).

EXAMPLE 10

N-[2-(4-Carbomethoxymethoxyphenyl)-1-methylethyl]-2-methoxy-2-phenylethanamine hydrochloride monohydrate The title compound, mp. 80°–3° C. (ethyl acetate), was obtained, as a 20:80 mixture of diastereoisomers, from 1-(4-carbomethoxymethoxyphenyl)propan-2-one and 2-methoxy-2-phenylethanamine by an analogous procedure to that described in Example 1.

$^1$H nmr δ(DMSO-d$_6$)

1.15 (3H, d), 2.6 (1H, m), 3.0–3.5 (9H, complex; 2H exchange with D$_2$O), 3.7 (3H, s), 4.6–4.85 (3H, s on m), 6.75–7.3 (4H, dd), 7.3–7.55 (5H, complex), 8.6–10.2 (2H, exchange with D$_2$O).

EXAMPLE 11

N-[2-(4-Methylaminocarbonylmethoxyphenyl)-1-methylethyl]-2-methoxy-2-phenylethanamine hydrochloride The title compound, mp. 175°–6° C. (methanol-ethyl acetate), was obtained, as a 67:33 mixture of diastereoisomers, from N-[2-(4-carbomethoxymethoxyphenyl)-1-methylethyl]-2-methoxy-2-phenylethanamine by an analogous procedure to that described in Example 4.

$^1$H nmr δ(DMSO-d$_6$)

1.15 (3H, d), 2.5–2.75 (4H, d on m), 2.95–3.5 (7H, complex), 4.4 (2H, s), 4.75 (1H, m), 6.8–7.3 (4H, dd), 7.3–7.5 (5H, complex), 8.1 (1H, exchanges with D$_2$O), 8.5–10.3 (2H, exchange with D$_2$O).

EXAMPLE 12

N-[2-(4-Carbomethoxymethoxyphenyl)-1-methylethyl]-2-methoxy-2-(3-bromophenyl)ethanamine hydrochloride The title compound, mp 155°–7° C. (methanol-ethyl acetate), was obtained as a 77:23 mixture of diastereoisomers, from 1-(4-carbomethoxymethoxyphenyl)propan-2-one and 2-methoxy-2-(3-bromophenyl)-ethanamine by an analogous procedure to that described in Example 1.

$^1$H nmr δ(DMSO-d$_6$) 1.1 (3H, d), 2.6 (1H, m), 3.0–3.55 (7H, complex), 3.65 (3H, s), 4.8–4.95 (3H, s on m), 6.75–7.3 (4H, dd), 7.3–7.7 (4H, complex), 8.5–10.3 (2H, exchange with D$_2$O).

EXAMPLE 13

N-[2-(4-(2-Methylaminoethoxy)phenyl)-1-methylethyl]-2-methoxy-2-phenylethanamine dihydrochloride The title compound, mp 257°–60° C. (methanol-ethyl acetate) was obtained, as a 77:23 mixture of diastereosiomers, from N-[2-(4-methylaminocarbonylmethoxyphenyl)-1-methylethyl]-2-methoxy-2-phenylethanamine by an analogous procedure to that described in Example 6.

$^1$H nmr δ(DMSO-d$_6$+CD$_3$OD)

1.15 (3H, d), 2.6–3.45 (13H, complex), 4.0–4.3 (2H, complex), 4.65 (1H, q), 6.9–7.3 (4H, dd), 7.4–7.5 (5H, s).

EXAMPLE 14

N-[3-(4-Carbomethoxymethoxyphenyl)-1-methylpropyl]-2-methoxy-2-(3-chlorophenyl)ethanamine hydrochloride The title compound, mp 92°–6° C. (ethyl acetate-diethyl ether), was obtained, as a 47:53 mixture of diastereoisomers, from 1-(4-carbomethoxymethoxyphenyl)-butan-3-one and 2-methoxy-2-(3-chlorophenyl)ethanamine by an analogous procedure to that described in Example 1.

$^1$H nmr δ(DMSO-d$_6$)

1.3 (3H, dd), 1.7–2.3 (2H, m), 2.6–2.8 (1H, m), 3.0–3.5 (7H, complex), 3.7 (3H, s), 4.7–4.9 (3H, s on m), 6.8–7.35 (4H, dd), 7.35–7.6 (4H, complex), 8.5–10.0 (2H, exchange with D$_2$O).

EXAMPLE 15

N-[2-(4-Methylaminocarbonylmethoxyphenyl)-1-methylethyl]-2-methoxy-2-(3-bromophenyl)ethanamine hydrochloride The title compound, mp 206°–8° C. (methanol-ethyl acetate), was obtained as a 63:37 mixture of diastereoisomers, from N-[2-(4-carbomethoxymethoxyphenyl)-1-methylethyl]-2-methoxy-2-(3-bromophenyl)ethanamine by an analogous procedure to that described in Example 4.

$^1$H nmr δ(DMSO-d$_6$)

1.15 (3H, d), 2.5–2.7 (4H, d on m), 3.0–3.45 (7H, complex), 4.4 (2H, s), 4.75 (1H, m), 6.8–7.3 (4H, dd), 7.3–7.7 (4H, complex), 8.05 (1H, exchange with D$_2$O), 8.5–9.7 (2H, exchange with D$_2$O).

EXAMPLE 16

N-[2-(4-Methylaminocarbonylmethoxyphenyl)-1-methylethyl]-2-ethoxy-2-(3-chlorophenyl)ethanamine hydrochloride The title compound, mp 157°–60° C. (methanol-ethyl acetate), was obtained as a 54:46 mixture of diastereoisomers, from N-[2-(4-carbomethoxymethoxyphenyl)-1-methylethyl]-2-ethoxy-2-(3-chlorophenyl)ethanamine hydrochloride by an analogous procedure to that described in Example 4.

$^1$H nmr δ(DMSO-d$_6$)

1.15 (6H, complex), 2.6–2.8 (4H, d on m), 3.0–3.5 (6H, complex), 4.4 (2H, s), 4.85 (1H, m), 6.8–7.3 (4H, dd), 7.3–7.55 (4H, complex), 8.05 (1H, exchanges with D$_2$O), 8.5–9.9 (2H, exchange with D$_2$O).

EXAMPLE 17

N-[2-(4-Methylaminoethoxy)phenyl)-1-methylethyl]-2-methoxy-2-(3-bromophenyl)ethanamine dihydrochloride The title compound, mp 268°–70° C. (methanol-ethyl acetate) was obtained, as a 71:29 mixture of diastereoisomers, from N-[2-(4-methylaminocarbonylmethoxyphenyl)-1-methyethyl]-2-methoxy-2-(3-bromophenyl)ethanamine by an analogous procedure to that described in Example 6.

$^1$H nmr δ(DMSO-d$_6$+CD$_3$OD)

1.2 (3H, d), 2.6–2.8 (4H, s on m), 3.0–3.5 (9H, complex), 4.0–4.4 (2H, complex), 4.7 (1H, m), 6.85–7.35 (4H, dd), 7.35–7.7 (4H, complex).

EXAMPLE 18

N-[2-(4-(2-Methylaminoethoxy)phenyl)-1-methylethyl]-2-ethoxy-2-(3-chlorophenyl)ethanamine dihydrochloride The title compound, mp 241°–2° C. (methanol-ethyl acetate), was obtained, as a 95:5 mixture of diastereoisomers, from N-[2-(4-methylaminocarbonylmethoxyphenyl)-1-methylethyl]-2-ethoxy-2-(3-chlorophenyl)ethanamine by an analogous procedure to that described in Example 6.

$^1$H nmr δ(DMSO-d$_6$)

1.2 (6H, complex), 2.6–2.8 (4H, s on m), 3.0–3.6 (8H, complex), 4.15–4.4 (2H, m), 4.9 (1H, m), 6.8–7.3 (4H, dd), 7.3–7.5 (4H, complex), 8.8–10.0 (4H, exchange with D$_2$O).

EXAMPLE 19

N-[2-(4-Dimethylaminocarbonylmethoxyphenyl)-1-methylethyl]-2-methoxy-2-(3-chlorophenyl)ethanamine hydrochloride The title compound, mp 185°–7° C. (methanol-ethyl acetate), was obtained, as a 88:12 mixture of diastereoisomers, from N-[2-(4-carbomethoxymethoxyphenyl)-1-methylethyl]-2-methoxy-2-(3-chlorophenyl)-ethanamine and 33% dimethylamine in industrial methylated spirits, by an analogous procedure to that described in Example 4.

$^1$H nmr δ(DMSO-d$_6$)

1.15 (3H, d), 2.5–3.6 (14H, complex), 4.65–4.95 (3H, s on m), 6.7–7.3 (4H, dd), 7.3–7.6 (4H, complex), 8.5–10.3 (2H, exchange with D$_2$O).

EXAMPLE 20

N-[2-(4-Aminocarbonylmethoxyphenyl)-1-methylethyl]-2-methoxy-2-(3-chlorophenyl)ethanamine The title compound was prepared, as an oil, from N-[2-(4-carbomethoxymethoxyphenyl)-1-methylethyl]-2-methoxy-2-(3-chlorophenyl)ethanamine and 0.88 ammonia, by an analogous procedure to that described in Example 4. The product was used in Example 24 without further purification.

EXAMPLE 21

N-[2-(4-(2-Hydroxyethoxy)phenyl)-1-methylethyl]-2-methoxy-2-phenylethanamine hydrochloride hemihydrate N-[2-(4-Carbomethoxymethoxyphenyl)-1-methylethyl]-2-methoxy-2-phenylethanamine (3.09 g) in dry tetrahydrofuran (30 ml) was added dropwise, with stirring, to a suspension of lithium aluminium hydride (1.65 g) in dry tetrahydrofuran (40 ml) and the resultant mixture heated under reflux for five hours. After cooling, water (1.7 ml), 10% aqueous sodium hydroxide (1.7 ml) and water (3.4 ml) were added carefully. Filtration and evaporation of the filtrate to dryness gave an oil which was converted to its hydrochloride salt by addition of ethereal hydrogen chloride. Crystallisation from methanol-ethyl acetate gave the title compound, mp 100°–2° C., as a 90:10 mixture of diastereoisomers.

$^1$H nmr δ(DMSO-d$_6$)

1.1 (3H, d), 2.5–2.75 (1H, m), 2.9 (9H, complex), 3.6–3.7 (1H, exchanges with D$_2$O), 3.9 (2H, t), 4.8 (2H, m; 1H exchanges with D$_2$O), 6.75–7.25 (4H, dd), 7.25–7.5 (5H, complex), 8.8 (1H, exchanges with D$_2$O), 9.8 (1H, exchanges with D$_2$O).

EXAMPLE 22

N-[3-(4-Methylaminocarbonylmethoxyphenyl)-1-methylpropyl]-2-methoxy-2-(3-chlorophenyl)ethanamine hydrochloride The title compound, mp 152°–4° C. (methanol-ethyl acetate), was obtained, as a 63:37 mixture of diastereoisomers, from N-[3-(4-carbomethoxymethoxyphenyl)-1-methylpropyl]-2-methoxy-2-(3-chlorophenyl)-ethanamine and methylamine, by an analogous procedure to that described in Example 4.

$^1$H nmr δ(DMSO-d$_6$)

1.3 (3H, dd), 1.65–2.3 (2H, m), 2.5–2.7 (4H, d on m), 3.0–3.5 (7H, complex), 4.4 (2H, s), 4.75 (1H, m), 6.8–7.3 (4H, dd), 7.35–7.5 (4H, complex), 8.05 (1H, exchanges with D$_2$O), 8.7 (1H, exchanges with D$_2$O), 9.6 (1H, exchanges with D$_2$O).

EXAMPLE 23

N-[2-(4-(2-Dimethylaminoethoxy)phenyl)-1-methylethyl]-2-methoxy-2-(3-chlorophenyl)ethanamine dihydrochloride hemihydrate The title compound, mp 233°–6° C. (methanol-ethyl acetate), was obtained from N-[2-(4-dimethylaminocarbonylmethoxyphenyl)-1-methylethyl]-2-methoxy-2-(3- chlorophenyl)ethanamine, by an analogous procedure to that described in Example 6.

$^1$H nmr δ(DMSO-d$_6$+D$_2$O)

1.1 (3H, d), 2.5–2.7 (1H, m), 2.75 (6H, s), 3.0–3.5 (9H, complex), 4.3 (2H, t), 4.8 (1H, m), 6.8–7.3 (4H, dd), 7.3–7.5 (4H, complex)

EXAMPLE 24

N-[2-(4-(2-Aminoethoxy)phenyl)-1-methylethyl]-2-methoxy-2-(3-chlorophenyl)ethanamine dihydrochloride hemihydrate The title compound, mp 236°–9° C. (methanol-ethyl acetate), was obtained as a 59:41 mixture of diastereoisomers, from N-[2-(4-aminocarbonylmethoxyphenyl)-1-methyl-ethyl]-2-methoxy-2-(3-chlorophenyl)ethanamine, by an analogous procedure to that described in Example 6.

$^1$H nmr δ(DMSO-d$_6$)

1.15 (3H, d), 2.5–2.8 (1H, m), 3.0–3.5 (9H, complex), 4.2 (2H, t), 4.85 (1H, m), 6.8–7.3 (4H, dd), 7.3–7.6 (4H, complex), 8.2–9.2 (5H, exchange with D$_2$O).

EXAMPLE 25

N-[2-(4-Carbomethoxymethoxyphenyl)-1-methylethyl]-2-$^n$-propoxy-2-(3-chlorophenyl)ethanamine hydrochloride The title compound, mp 104°–8° C. (ethyl acetate-hexane), was obtained, as a 62:38 mixture of diastereoisomers, from 1-(4-carbomethoxymethoxyphenyl)propan-2-one and 2-$^n$propoxy-2-(3-chlorophenyl)ethanamine, by an analogous procedure to that described in Example 1.

$^1$H nmr δ(DMSO-d$_6$)

0.85 (3H, t), 1.15 (3H, m), 1.4–1.7 (2H, m), 2.5–2.75 (1H, m), 2.95–3.5 (6H, complex), 3.65 (3H, s), 4.7 (2H, s), 4.85 (1H, m), 6.8–7.25 (4H, dd), 7.25–7.5 (4H, complex), 8.8, 9.8 (2H, exchange with D$_2$O).

EXAMPLE 26

N-[2-(4-Carbomethoxymethoxyphenyl)-1-methylethyl]-2-isopropoxy-2-(3-chlorophenyl)ethanamine hydrochloride The title compound, mp 134°–7° C. (ethyl acetate-hexane), was obtained, as a 55:45 mixture of diastereoisomers, from 1-(4-carbomethoxymethoxyphenyl)propan-2-one and 2-isopropoxy-2-(3-chlorophenyl)ethanamine, by an analogous procedure to that described in Example 1.

$^1$H nmr δ(DMSO-d$_6$)

0.9–1.4 (9H, complex), 2.5–2.8 (1H, m), 3.0–3.6 (5H, complex), 3.7 (3H, s), 4.75 (2H, s), 5.2 (1H, m), 6.8–7.3 (4H, dd), 7.3–7.6 (4H, complex), 8.8, 10.1 (2H, exchange with D$_2$O).

EXAMPLE 27

N-[2-(4-Methylaminocarbonylmethoxyphenyl)-1-methylethyl]-2-$^n$propoxy-2-(3-chlorophenyl)ethanamine dihydrochloride hemihydrate The title compound, mp 108°–114° C. (methanol-ethyl acetate-hexane), was obtained, as a 63:37 mixture of diastereoisomers, from N-[2-(4-carbomethoxymethoxyphenyl)-1-methylethyl]-2-$^n$propoxy-2-(3-chlorophenyl)ethanamine, by an analogous procedure to that described in Example 4.

$^1$H nmr δ(DMSO-d$_6$)

0.85 (3H, t), 1.15 (3H, d), 1.5 (2H, m), 2.5–2.75 (4H, d on m), 3.0–3.5 (6H, complex), 4.4 (2H, s), 4.8 (1H, m), 6.8–7.3 (4H, dd), 7.3–7.55 (4H, complex), 8.0, 8.7, 9.5 (3H, all exchange with D$_2$O).

EXAMPLE 28

N-[2-(4-Methylaminocarbonylmethoxyphenyl)-1-methylethyl]-2-isopropoxy-2-(3-chlorophenyl)ethanamine dihydrochloride hemihydrate The title compound, mp 116°–128° C. (methanol-ethylacetate-diethyl ether), was obtained, as a 63:37 mixture of diastereoisomers, from N-[2-(4-carbomethoxymethoxyphenyl)-1-methylethyl]-2-isopropoxy-2-(3-chlorophenyl)ethanamine, by an analogous procedure to that described in Example 4.

$^1$H nmr δ(DMSO-d$_6$)

0.9–1.4 (9H, complex), 2.5–2.85 (4H, complex), 3.0–3.7 (5H, complex), 4.45 (2H, s), 5.15 (1H, m), 6.8–7.2 (4H, dd), 7.2–7.65 (4H, complex), 8.2, 8.8, 10.0 (3H, all exchange with D$_2$O).

EXAMPLE 29

N-[2-(4-(2-Methylaminoethoxy)phenyl)-1-methylethyl]-2-$^n$propoxy-2-(3-chlorophenyl)ethanamine dihydrochloride The title compound, mp 220°–3° C. (methanol-ethyl acetate), was obtained, as a 59:41 mixture of diastereoisomers, from N-[2-(4-methylaminocarbonylmethoxyphenyl)-1-methylethyl]-2-$^n$propoxy-2-(3-chlorophenyl)ethanamine, by an analogous procedure to that described in Example 6.

$^1$H nmr δ(DMSO-d$_6$)

0.85 (3H, t), 1.2 (3H, complex), 1.55 (2H, m), 2.5–2.8 (4H, s on m), 3.0–3.65 (8H, complex), 4.3 (2H, m), 5.0 (1H, m), 6.8–7.3 (4H, dd), 7.35–7.6 (4H, complex), 9.6 (4H, exchange with D$_2$O).

EXAMPLE 30

N-[2-(4-N'-Methylcarboxamidophenyl)-1-methylethyl]-2-methoxy-2-(3-chlorophenyl)ethanamine hydrochloride The title compound, mp 228°–30° C. (methanol-ethyl acetate-diethyl ether), was obtained, as a 69:31 mixture of diastereoisomers from N-[2-(4-carbomethoxyphenyl)-1-methylethyl]-2-methoxy-2-(3-chlorophenyl)ethanamine by an analogous procedure to that described in Example 4.

$^1$H nmr δ(DMSO-d$_6$)

1.15 (3H, d); 2.6–3.6 (11H, complex); 4.8 (1H, m); 7.2–7.6 (6H, complex); 7.7–7.9 (2H, d); 8.5, 8.95, 10.0 (3H, exchange with D$_2$O).

EXAMPLE 31

N-[2-(4-Hydroxymethylphenyl)-1-methylethyl]-2-methoxy-2-(3-chlorophenyl)ethanamine hydrochloride The title compound, mp 151°–5° C. (methanol-ethyl acetate-diethyl ether), was obtained, as a 87:13 mixture of diastereoisomers, from N-[2-(4-carbomethoxyphenyl)-1-methylethyl]-2-methoxy-2-(3-chlorophenyl)ethanamine, by an analogous procedure to that described in Example 21.

$^1$H nmr δ(DMSO-d$_6$)

1.15 (3H, d); 2.5–2.75 (1H, m); 3.0–3.7 (7H, complex); 4.5 (2H, d; s on m, D$_2$O exchange), 4.8 (1H, m); 5.2 (1H, exchanges with D$_2$O); 7.1–7.6 (8H, complex); 8.5–10.2 (2H, exchange with D$_2$O).

EXAMPLE 32

N-[2-(4-Carbomethoxyphenyl)-1-methylethyl]-2-methoxy-2-phenylethanamine hydrochloride hemihydrate The title compound, mp 178°–85° C. (ethyl acetate-diethyl ether-hexane), was obtained, as a 59:41 mixture of diastereoisomers, from 1-(4-carbomethoxyphenyl)-propan-2-one and 2-methoxy-2-phenylethanamine, by an analogous procedure to that described in Example 5.

$^1$H nmr δ(DMSO-d$_6$)

1.15 (3H, complex); 2.55–3.6 (8H, complex); 3.75 (3H, s); 4.8 (1H, m); 7.1–7.6 (7H, complex); 7.7–7.95 (2H, d); 8.9, 10.4 (2H, exchange with D$_2$O).

EXAMPLE 33

N-[2-(4-Carbomethoxyphenyl)-1-methylethyl]-2-ethoxy-2-(3-chlorophenyl)ethanamine hydrochloride hemihydrate The title compound, mp 74°–9° C. (methanol-ethyl acetate-hexane), was obtained, as a 90:10 mixture of diastereoisomers from 1-(4-carbomethoxyphenyl)propan-2-one and 2-ethoxy-2-(3-chlorophenyl)ethanamine, by an analogous procedure to that described in Example 5.

$^1$H nmr δ(DMSO-d$_6$)

0.9–1.3 (6H, complex); 2.55–3.6 (7H, complex); 3.8 (3H, s); 4.9 (1H, m); 7.2–7.6 (6H, complex); 7.8–8.0 (2H, d); 8.9, 10.05 (2H, exchange with D$_2$O).

EXAMPLE 34

N-[2-(4-N'-Methylcarboxamidophenyl)-1-methylethyl]-2-ethoxy-2-(3-chlorophenyl)ethanamine hydrochloride The title compound, mp 209°–214° C. (methanol-ethyl acetate-diethyl ether), was obtained, as a 75:25 mixture of diastereoisomers, from N-[2-(4-carbomethoxyphenyl)-1-methylethyl]-2-ethoxy-2-(3-chlorophenyl)-ethanamine, by an analagous procedure to that described in Example 4.

$^1$H nmr δ(DMSO-d$_6$)

1.0–1.3 (6H, complex); 2.6–3.7 (10H, complex); 4.95 (1H, m); 7.2–7.55 (6H, complex); 7.7–7.9 (2H, d); 8.5, 8.95, 10.0 (3H, exchange with D$_2$O).

EXAMPLE 35

N-[2-(4-N'-Methylaminomethylphenyl)-1-methylethyl]-2-methoxy-2-(3-chlorophenyl)ethanamine dihydrochloride The title compound, mp 238°–245° C. (methanol-ethyl acetate-diethyl ether) was obtained, as a 76:24 mixture of diastereoisomers, from N-[2-(4-N'-methylcarboxamido-phenyl)-1-methylethyl]-2-methoxy-2-(3-chlorophenyl)ethanamine, by an analogous procedure to that described in Example 6. $^1$H nmr δ(DMSO-d$_6$+D$_2$O)

1.15 (3H, d); 2.6–3.6 (13H, complex); 4.9 (1H, m); 7.2–7.9 (8H, complex)

EXAMPLE 36

N-[2-(4-Carbomethoxymethoxyphenyl)-1-methylethyl]-2-methoxy-2-(2-benzofuranyl)ethanamine hydrochloride The title compound, mp 149°–151° C. (methanol-ethyl acetate-hexane), was obtained, as a 62:38 mixture of diastereoisomers from 1-(4-carbomethoxymethoxyphenyl)-propan-2-one and 2-methoxy-2-(2-benzofuranyl)ethanamine by an analogous procedure to that described in Example 1.

$^1$H nmr δ(DMSO-d$_6$)

1.2 (3H, d); 2.5–2.8 (1H, m); 3.1–3.55 (7H, complex); 3.75 (3H, s); 4.8 (2H, s); 5.2 (1H, m); 6.85–7.9 (9H, complex); 9.2, 10.4 (2H, exchange with D$_2$O).

EXAMPLE 37

N-[2-(4-Methylaminocarbonylmethoxyphenyl)-1-methylethyl]-2-methoxy-2-(2-benzofuranyl)ethanamine dihydrochloride The title compound, mp 138°–142° C. (methanol-ethyl acetate) was obtained, as a 73:27 mixture of diastereoisomers, from N-[2-(4-carbomethoxymethoxyphenyl)-1-methylethyl]-2-methoxy-2-(2-benzofuranyl)-ethanamine, by an analogous procedure to that described in Example 4.

$^1$H nmr δ(DMSO-d$_6$+D$_2$O)

1.15 (3H, d); 2.5–2.8 (4H, d on m); 3.1–3.7 (7H, complex); 4.45 (2H, s); 5.15 (1H, m); 6.7–7.8 (9H, complex).

EXAMPLE 38

N-[2-(4-Methoxyphenyl)-1-methylethyl]-2-methoxy-2-(3-chlorophenyl)ethanamine hydrochloride The title compound, m.p. 163°–5° C. (methanol-ethyl acetate), was obtained as a 76:24 mixture of diastereoisomers, from 1-(4-methoxyphenyl)propan-2-one and 2-methoxy-2-(3-chlorophenyl)ethanamine by an analogous procedure to that described in Example 1.

$^1$H nmr δ(DMSO-d$_6$)

1.1 (3H, d), 2.5 (1H, m), 2.8–3.4 (7H, s on m), 3.6 (3H, s), 4.8 (1H, m), 6.7–7.2 (4H, dd), 7.2–7.5 (4H, complex), 8.8–10 (2H, broad; exchange with D$_2$O).

EXAMPLE 39

N-[2-(3-Methoxyphenyl)-1-methylethyl]-2-methoxy-2-(3-chlorophenyl)ethanamine hydrochloride The title compound, m.p. 109°–11° C. (ethylacetate-diethyl ether hexane), was obtained as a 63:37 mixture of diastereoisomers, from 1-(3-methoxyphenyl)propan-2-one and 2-methoxy-2-(3-chlorophenyl)ethanamine by an analogous procedure to that described in Example 1.

$^1$H nmr δ(DMSO-d$_6$)

1.2 (3H, complex), 2.6 (1H, m), 2.9–3.6 (7H, complex), 3.7 (3H, s), 4.9 (1H, m), 6.7–7.6 (8H, complex), 8.7–10.3 (2H, exchange with D$_2$O).

EXAMPLE 40

N-[2-(4-Isopropylthiophenyl)-1-methylethyl]-2-methoxy-2-(3-chlorophenyl)ethanamine hydrochloride 1-(4-Isopropylthiophenyl)propan-2-one (4.16 g) and 2-methoxy-2-(3-chlorophenyl)ethanamine (3.71 g) in dry benzene (100 ml) was boiled under reflux for two hours in an apparatus incorporating a water trap. The solution was cooled and the solvent removed under reduced pressure. The residue was dissolved in ethanol (80 ml), cooled to less than 10° C. and treated portionwise with sodium borohydride (3.0 g) over 30 minutes. The mixture was stirred for one hour and the solvent removed under reduced pressure. The residue was dissolved in dichloromethane, washed with water, dried over magnesium sulphate, filtered and evaporated. Chromatography of the residue on silica gel in 2–4% methanol-dichloromethane gave an oil which was converted to its hydrochloride salt by addition of ethereal hydrogen chloride. Crystallisation from methanol-ethyl acetate-hexane gave the title compound, m.p. 133°–9° C., as a 70:30 mixture of diastereoisomers.

$^1$H nmr δ(DMSO-d$_6$)
0.9–1.35 (9H, complex), 2.5–3.6 (9H, complex), 4.8 (1H, m), 7.05–7.55 (8H, complex), 8.95, 10.2 (2H, exchange with D$_2$O).

EXAMPLE 41

N-[2-(4-Dimethylaminophenyl)-1-methylethyl]-2-methoxy-2-(3-chlorophenyl)ethanamine dihydrochloride hemihydrate The title compound, m.p. 220°–4° C. (methanol-ethyl acetate), was obtained as a 65:35 mixture of diastereoisomers, from 1-(4-dimethylaminophenyl)propan-2-one and 2-methoxy-2-(3-chlorophenyl)ethanamine by an analogous procedure to that described in Example 40.

$^1$H nmr δ(DMSO-d$_6$+D$_2$O)
1.1 (3H, d), 2.6–3.6 (14H, complex), 4.7 (1H, m), 7.3–7.7 (8H, complex).

EXAMPLE 42

N-[2-(4-Carbomethoxymethoxyphenyl)-1-methylethyl]-2-$^n$butoxy-2-(3-chlorophenyl)ethanamine hydrochloride The title compound, m.p. 87°–94° C. (ethyl acetate-diethyl ether) was obtained as a 60:40 mixture of diastereoisomers, from 1-(4-carbomethoxymethoxyphenyl)-propan-2-one and 2-$^n$butoxy-2-(3-chlorophenyl)ethanamine, by an analogous procedure to that described in Example 1.

$^1$H nmr δ(DMSO-d$_6$)
0.8 (3H, t), 1.0–1.7 (7H, complex). 2.5–2.8 (1H, m), 2.9–3.6 (6H, complex), 3.7 (3H, s), 4.75 (2H, s), 4.95 (1H, m), 6.8–7.3 (4H, dd), 7.3–7.6 (4H, complex), 8.9, 10.0 (2H, exchange with D$_2$O).

EXAMPLE 43

N-[2-(4-Methylaminocarbonylmethoxyphenyl)-1-methylethyl]-2-$^n$butoxy-2-(3-chlorophenyl)ethanamine hydrochloride hemihydrate The title compound, m.p. 130°–7° C. (ethyl acetate-diethyl ether), was obtained as a 52:48 mixture of diastereoisomers, from N-[2-(4-carbomethoxymethoxyphenyl)-1-methylethyl]-2-$^n$butoxy-2-(3-chlorophenyl)ethanamine, by an analogous procedure to that described in Example 4.

$^1$H nmr δ(DMSO-d$_6$)
0.8 (3H, t), 1.0–1.7 (7H, complex). 2.55–2.85 (4H, complex), 2.9–3.7 (6H, complex). 4.45 (2H, s), 5.0 (1H, m), 6.8–7.3 (4H, dd), 7.3–7.6 (4H, complex), 8.0–10.2 (4H, exchange with D$_2$O).

EXAMPLE 44

N-[2-(4-Carbomethoxymethoxyphenyl)-1-methylethyl]-2-$^n$hexyloxy-2-(3-chlorophenyl)ethanamine hydrochloride The title compound, m.p. 85°–92° C. (diethylether), was obtained as a 64:36 mixture of diastereoisomers, from 1-(4-carbomethoxymethoxyphenyl)propan-2-one and 2-$^n$hexyloxy-2-(3-chlorophenyl)ethanamine, by an analogous procedure to that described in Example 1.

$^1$H nmr δ(DMSO-d$_6$)
0.65–1.75 (14H, complex), 2.6–2.9 (1H, m), 3.0–3.7 (6H, complex), 3.75 (3H, s), 4.8 (2H, s), 5.05 (1H, m), 6.8–7.3 (4H, dd), 7.3–7.6 (4H, complex), 9.1, 10.3 (2H, exchange with D$_2$O).

EXAMPLE 45

N-[2-(4-Carbomethoxyphenyl)-1-methylethyl]-2-methoxy-2-(3-trifluoromethylphenyl)ethanamine hydrochloride hemihydrate The title compound, m.p. 180°–3° C. (methanol-diethyl ether), was obtained, as a 76:24 mixture of diastereoisomers, from 1-(4-carbomethoxyphenyl)propan-2-one and 2-methoxy-2-(3-trifluoromethylphenyl)ethanamine, by an analogous procedure to that described in Example 5.

$^1$H nmr δ(DMSO-d$_6$+D$_2$O)
1.2 (3H, d), 2.6–2.95 (1H, m), 3.0–3.7 (7H, complex). 3.8 (3H, s), 5.0 (1H, m), 7.3–8.0 (8H, complex).

EXAMPLE 46

N-[2-(4-(2-Methylaminoethoxy)phenyl)-1-methylethyl]-2-methoxy-2-(3-trifluoromethylphenyl)ethanamine dihydrochloride The title compound, m.p. 258°–60° C. (methanol-ethyl acetate), was obtained, as a 60:40 mixture of diastereoisomers, from N-[2-(4-methylaminocarbonylmethoxyphenyl)-1-methylethyl]-2-methoxy-2-(3-trifluoromethylphenyl)ethanamine, by an analogous procedure to that described in Example 6.

$^1$H nmr δ(DMSO-d$_6$)
1.15 (3H, complex), 2.6–2.8 (4H, s on m), 3.0–3.6 (9H, complex), 4.3 (2H, m), 5.0 (1H, m), 6.85–7.35 (4H, dd), 7.65–7.9 (4H, complex), 9.0–10.0 (4H, exchange with D$_2$O).

EXAMPLE 47

N-[2-(4-{[E]-2-Carbomethoxyethenyl}phenyl)-1-methylethyl]-2-methoxy-2-(3-chlorophenyl)ethanamine hydrochloride The title compound, m.p. 148°–50° C. (ethyl acetate-hexane), was obtained as a 78:22 mixture of diastereoisomers, from 4-[E]-(2-carbomethoxyethenyl)phenylpropan-2-one and 2-methoxy-2-(3-chlorophenyl)ethanamine, by an analogous procedure to that described in Example 40.

$^1$H nmr δ(DMSO-d$_6$)
1.2 (3H, d), 2.6–3.6 (8H, complex), 3.8 (3H, s), 4.95 (1H, m), 6.6 (1H, d), 7.1–7.9 (9H, complex), 9.1, 10.2 (2H, exchange with D$_2$O).

EXAMPLE 48

N-[2-{4-(2-Hydroxyethoxy)phenyl}-1-methylethyl]-2-methoxy-2-(3-chlorophenyl)ethanamine hydrobromide The title compound, m.p. 138°–140° C. (methanol-ethyl acetate-diethyl ether), was obtained as a mixture of diastereoisomers, from N-[2-(4-carbomethoxymethoxyphenyl)-1-methylethyl]-2-methoxy-2-(3-chlorophenyl)ethanamine, by an analogous procedure to that described in Example 21.

$^1$H nmr δ(DMSO-d$_6$+D$_2$O)
1.15 (3H, d), 2.55–2.80 (1H, m), 3.0–3.5 (7H, complex), 3.6–3.8 (2H, m), 3.85–4.05 (2H, m), 4.7 (1H, m), 6.8–7.3 (4H, dd), 7.35–7.6 (4H, complex).

EXAMPLE 49

N-[2-(4-Carbomethoxymethylphenyl)-1-methylethyl]-2-methoxy-2-(3-chlorophenyl)ethanamine hydrochloride The title compound, m.p. 138°–47° C. (ethyl acetate-diethyl ether) was obtained, as a 57:43 mixture of diastereoisomers from 1-(4-carbomethoxymethyl)propan-2-one and 2-methoxy-2-(3-chlorophenyl)ethanamine by an analogous procedure to that described in Example 1.

$^1$H nmr δ(DMSO-d$_6$)

1.2 (3H, m), 2.6–2.9 (1H, m), 3.0–3.55 (7H, complex), 3.6–3.7 (5H, two singlets), 4.9 (1H, m), 7.15–7.65 (8H, complex), 9.0, 10.2 (2H, exchange with D$_2$O).

EXAMPLE 50

N-[2-(4-Carbomethoxymethoxyphenyl)-1-methylethyl]-2-benzyloxy-2-(3-chlorophenyl)ethanamine hydrochloride The title compound, m.p. 86°–94° C. (diethyl ether), was obtained as a 92:8 mixture of diastereoisomers, from 1-(4-carbomethoxymethoxyphenyl)propan-2-one and 2-benzyloxy-2-(3-chlorophenyl)ethanamine, by an analogous procedure to that described in Example 1.

$^1$H nmr δ(DMSO-d$_6$)

1.15 (3H, d), 2.55–2.85 (1H, m), 3.0–3.55 (4H, complex), 3.8 (3H, s), 4.2–4.75 (2H, dd), 4.8 (2H, s), 5.2 (1H, m), 6.8–7.7 (13H, complex), 9.1, 10.1 (2H, exchange with D$_2$O).

EXAMPLE 51

N-[2-(4-Methylaminocarbonylmethoxyphenyl)ethyl]-2-methoxy-2-(3-chlorophenyl)ethanamine hydrochloride A mixture of 2-methoxy-2-(3-chlorophenyl)ethanamine (1.81 g), 2-(4-carbomethoxymethoxyphenyl)-1-(p-toluenesulphonyloxy)ethane (4.0 g) and triethylamine (4 ml) in dimethyl sulphoxide (50 ml) was heated at 55° C. After 24 h the solution was poured into saturated sodium carbonate solution and the aqueous layer extracted with dichloromethane. The organic extract was separated, dried and evaporated. Chromatography over silica gel (eluting with 2% methanol-dichloromethane) gave N-[2-(4-carbomethoxymethoxyphenyl)ethyl]-2-methoxy-2-(3-chlorophenyl)ethanamine which was converted into the title compound, mp 167°–169° C. (ethyl acetate-hexane) by an analogous procedure to that described in Example 4.

$^1$H nmr δ(DMSO-d$_6$)

2.5–2.7 (3H, m), 2.8–3.4 (6H, m), 3.25 (3H, s), 4.4 (2H, s), 4.75 (1H, t), 6.9 (2H, d), 7.2 (2H, d), 7.3–7.6 (4H, m), 7.9–8.2 (1H, brd.m), 9.1–9.8 (2H, brd.m, exchanges with D$_2$O).

EXAMPLE 52

N-[2-(4-Methylaminocarbonylmethoxyphenyl)-1-methylethyl]-2-methoxy-3-phenoxypropanamine hydrochloride The title compound, mp 213°–215° C. (methanol-ethyl acetate) was obtained, as a 11:89 mixture of diastereoisomers, from 2-methoxy-3-phenoxypropanamine and 1-(4-carbomethoxymethoxyphenyl)propan-2-one by an analogous procedure to that described in Examples 1 and 4.

$^1$H nmr δ(DMSO-d$_6$/D$_2$O)

1.2 (3H, d), 2.6–2.8 (4H, m), 3.1–3.5 (4H, m), 3.55 (3H, s), 4.0–4.3 (3H, m), 4.5 (2H, s), 6.8–7.5 (9H, m).

EXAMPLE 53

N-[2-(4-Carbomethoxymethoxyphenyl)-1-methyl ethyl]-2-methoxy-2-(2,3-difluorophenyl)ethanamine 1-(4-Carbomethoxymethoxyphenyl)propan-2-one (2.20 g) and 2-methoxy-2-(2,3-difluorophenyl)ethanamine (1.87 g) in methanol (50 ml) was hydrogenated in the presence of platinum (from platinum oxide, 50 mg) until hydrogen uptake ceased. The solution was filtered through diatomaceous earth, and the solvent removed under reduced pressure. Chromatography of the residue on silica-gel eluting with 2% methanol in dichloromethane gave the title compound as an oil. The product was used in Example 54 without further purification.

EXAMPLE 54

N-[2-(4-Methylaminocarbonylmethoxyphenyl)-1-methylethyl]-2-methoxy-2-(2,3-difluorophenyl)ethanamine dihydrochloride The title compound, m.p. 134°–39° C. (methanol-ethyl acetate-diethyl ether) was obtained as a 62:38 mixture of diastereoisomers from N-[2-(4-carbomethoxymethoxyphenyl)-1-methylethyl]-2-methoxy-2-(2,3-difluorophenyl)ethanamine, by an analogous procedure to that described in Example 4.

$^1$H nmr δ(DMSO-d$_6$+D$_2$O)

1.15 (3H, d); 2.65 (3H, s); 3.0–3.7 (5H, m); 3.26 (3H, s); 4.43 (2H, s); 5.10 (1H, q); 6.91 (2H, d); 7.20 (2H, d); 7.3–7.7 (3H, m).

EXAMPLE 55

N-[2-(4-Methylaminocarbonylmethoxyphenyl)-1-methylethyl]-2-methoxy-2-(2-fluorophenyl)ethanamine hydrochloride The title compound m.p. 164°–8° C. (methanol-ethyl acetate) was obtained from 1-(4-carbomethoxymethoxyphenyl)propan-2-one and 2-methoxy-2-(2-fluorophenyl)ethanamine by an analogous procedure to that described in Examples 53 and 54.

$^1$H nmr δ(DMSO-d$_6$+D$_2$O)

1.12 (3H, d); 2.66 (3H, d); 3.0–3.6 (5H, m); 3.23 (3H, s); 4.41 (2H, s); 5.00 (1H, q); 6.90 (2H, d); 7.19 (2H, d); 7.2–7.6 (4H, m).

EXAMPLE 56

N-[2-(4-Methylaminocarbonylmethoxyphenyl)-1-methylethyl]-2-methoxy-2-(3-methylphenyl)ethanamine hydrochloride The title compound m.p. 180°–3° C. (methanol-ethyl acetate) was obtained as a 37:63 mixture of diastereoisomers from 1-(4-carbomethoxymethoxyphenyl)propan-2-one and 2-methoxy-2-(3-methylphenyl)ethanamine by an analogous procedure to that described in Examples 53 and 54.

$^1$H nmr δ(DMSO-d$_6$+D$_2$O)

1.18 (3H, d); 2.34 (3H, s); 2.68 (3H, s); 2.6–2.9 (1H, m); 3.0–3.6 (4H, m); 3.23 (3H, s); 4.43 (2H, s); 4.6–4.9 (1H, m); 6.92 (2H, d); 7.1–7.5 (6H, m).

EXAMPLE 57

N-[2-(4-(2-Phenoxyethoxy)phenyl)-1-methylethyl]-2-methoxy-2-(3-chlorophenyl)ethanamine hydrochloride The title compound m.p. 145°–9° C. (ethyl acetate-diethyl ether) was obtained as a 10:90 mixture of diastereoisomers from 1-(4-[2-phenoxyethoxy]phenyl)propan-2-one (1.80 g) and 2-methoxy-2-(3-chlorophenyl)ethanamine (0.7 g) by an analogous procedure to that described in Example 53.

$^1$H nmr δ(DMSO-d$_6$+D$_2$O)

1.10 (3H, d); 2.6–2.9 (1H, m); 3.0–3.5 (4H, m); 3.22 (3H, s); 4.29 (4H, s); 4.6–4.9 (1H, m); 6.8–7.6 (13H, m).

EXAMPLE 58

N-[2-(4-N'-Methyl-N'-carbomethoxymethylaminophenyl)-1-methylethyl]-2-methoxy-2-phenylethanamine dihydrochloride The title compound m.p. 191°–4° C. (methanol-ethyl acetate-diethyl ether) was obtained as a 66:34 mixture of diastereoisomers from 1-(4-N-methyl-N-carbomethoxymethylaminophenyl)propan-2-one (1.70 g) and 2-methoxy-2-phenylethanamine (1.06 g) by an analogous procedure to that described in Example 53.

$^1$H-nmr $\delta$(DMSO-d$_6$+D$_2$O)

1.14 (3H, d); 2.98 (3H, s); 3.0–3.6 (5H, m); 3.20 (3H, s); 3.62 (3H, s); 4.19 (2H, m); 4.5–4.8 (1H, m); 6.74 (2H, d); 7.08 (2H, d); 7.3–7.6 (5H, m).

EXAMPLE 59

N-[2-(4-(2-Methylaminoethoxy)phenyl)-1-(R)-1-methylethyl]-2-(R)-2-methoxy-2-phenylethanamine dihydrochloride hemihydrate The title compound, mp 262°–3° C., $[\alpha]_D^{20}$(c=1)=−57.2° (methanol), was obtained, as a 97:3 mixture of diastereoisomers, from N-[2-(4-methylaminocarbonylmethoxyphenyl)-1-(R)-1-methylethyl]-2-(R)-2-methoxy-2-phenylacetamide (1.2 g) and borane-methyl sulphide complex (8 ml) by an analogous procedure to that described in Example 6.

EXAMPLE 60

N-[2-(4-Carbomethoxymethoxyphenyl)-1-methylethyl]-2-methoxy-2-(3-chlorophenyl)ethanamine hydrochloride(RR,SS)diasteroisomer Recrystallisation of the product described in Example 1, from methanol-ethyl acetate, gave the title compound, mp 158°–9° C., of 98% diastereoisomeric purity.

EXAMPLE X1

1-Methoxy-1-(3-chlorophenyl)acetonitrile

A solution of 3-chlorobenzaldehyde dimethylacetal (10.25 g) and trimethylsilylcyanide (10 ml) in dry ether (20 ml) was added dropwise to a solution of boron trifluoride-diethyl etherate (0.6 ml) in dry ether (10 ml) with stirring at room temperature. The resulting mixture was stirred at room temperature for 21 hours, diluted with ether (100 ml), washed twice with saturated sodium bicarbonate solution, once with brine, dried (magnesium sulphate), filtered and the solvent removed under reduced pressure to give 1-methoxy-1-(3-chlorophenyl)acetonitrile as an oil b.p. 106°–110° C./0.8 mm.

$^1$H nmr $\delta$CDCl$_3$ 3.6 (3H, s); 5.2 (1H, s); 7.4–7.6 (4H, complex)

EXAMPLE X2

2-Methoxy-2-(3-chlorophenyl)ethanamine

A solution of 1-methoxy-1-(3-chlorophenyl)acetonitrile (8 g) in dry diethyl ether (30 ml) was added dropwise to a stirred suspension of lithium aluminium hydride (4 g) in dry diethyl ether (100 ml). The mixture was boiled under reflux for 2 hours, cooled and water (4 ml) 10% sodium hydroside solution (6 ml) and water (8 ml), was added sequentially. The precipitate was filtered, washed with diethyl ether-dichloromethane and the combined filtrate was dried over magnesium sulphate. Filtration and evaporation gave 2-methoxy-2-(3-chlorophenyl)ethanamine, which was used without further purification.

$^1$H nmr $\delta$(CDCl$_3$)

1.55 (2H, broad s, exchange with D$_2$O); 2.80 (2H, d); 3.3 (3H, s); 4.15 (1H, t); 7.2 (4H, complex).

EXAMPLE X3

1-Methoxy-1-(3-trifluoromethylphenyl)acetonitrile 1-methoxy-1-(3-trifluoromethylphenyl)acetonitrile, b.p. 90°–94° C./0.6 mm, was prepared from 3-trifluoromethylbenzaldehyde-dimethyl acetal by an analogous procedure to that described in Example X1.

$^1$H nmr $\delta$(CDCl$_3$)

3.6 (3H, s); 5.2 (1H, s); 7.4–7.8 (4H, complex)

EXAMPLE X4

2-Methoxy-2-(3-trifluoromethylphenyl)ethanamine

2-Methoxy-2-(3-trifluoromethylphenyl)ethanamine was prepared as an oil by an analogous procedure to that described in Example X2 and was used without further purification.

$^1$H nmr $\delta$(CDCl$_3$)

1.3 (2H, broad singlet, exchange with D$_2$O); 2.8 (2H, d); 3.3 (3H, s); 4.15 (1H, t); 7.4 (4H, complex)

EXAMPLE X5

1-Ethoxy-1-(3-chlorophenyl)acetonitrile

1-Ethoxy-1-(3-chlorophenyl)acetonitrile b.p. 116°–8° C./0.8 mm was prepared from 3-chlorobenzaldehyde diethyl acetal by an analogous procedure to that described in Example X1.

$^1$H nmr $\delta$(CDCl$_3$)

1.3 (3H, t); 3.7 (2H, m); 5.2 (1H, s); 7.3–7.5 (4H, complex).

EXAMPLE X6

2-Ethoxy-2-(3-chlorophenyl)ethanamine

2-Ethoxy-2-(3-chlorophenyl)ethanamine was prepared as an oil by an analogous procedure to that described in Example X2 and was used without further purification.

$^1$H nmr $\delta$(CDCl$_3$)

1.2 (3H, t); 1.5 (2H, broad singlet, exchange with D$_2$O); 2.8 (2H, d); 3.4 (2H, quartet); 4.2 (1H, t); 7.2 (4H, complex).

EXAMPLE X7

2-Methoxy-2-(3-bromophenyl)ethanamine

1-Methoxy-1-(3-bromophenyl)acetonitrile was prepared from 3-bromobenzaldehyde dimethyl acetal and trimethylsilyl cyanide, using zinc iodide as catalyst, by an analogous procedure to that described in Example X1. Reduction of the acetonitrile with lithium aluminium hydride by an analogous procedure to that described in Example X2 gave the title compound.

$^1$H nmr $\delta$(CDCl$_3$)

1.4 (2H, broad s); 2.9 (2H, d); 3.3 (3H, s); 4.1 (1H, t); 7.15–7.6 (4H, complex).

EXAMPLE X8

2-Methoxy-2-phenylethanamine

The title compound was prepared from benzaldehyde dimethyl acetal via 1-methoxy-1-phenylacetonitrile by an analogous procedure to that described in Example X7.

¹H nmr δ(CDCl₃)
1.4 (2H, s); 2.85 (2H, d); 3.3 (3H, s); 4.15 (1H, t); 7.3 (5H, s).

EXAMPLE X9

2-ⁿPropoxy-2-(3-chlorophenyl)ethanamine

The title compound was prepared from 3-chlorobenzaldehyde di-ⁿpropyl acetal via 1-ⁿpropoxy-1-(3-chlorophenyl)acetonitrile by an analogous procedure to that described in Example X7.

¹H nmr δ(CDCl₃)
0.95 (3H, t); 1.3–1.9 (5H, m); 2.8 (2H, d); 3.3 (2H, t); 4.15 (1H, t); 7.0–7.4 (4H, complex).

EXAMPLE X10

2-Isopropoxy-2-(3-chlorophenyl)ethanamine

The title compound was prepared from 3-chlorobenzaldehyde di-isopropyl acetal via 1-isopropoxy-1-(3-chlorophenyl)acetonitrile by an analogous procedure to that described in Example X7.

¹H nmr δ(CDCl₃)
1.15 (6H, two d); 1.5 (2H, broad s); 2.75 (2H, d); 3.5 (1H, m); 4.3 (1H, t); 7.1–7.4 (4H, complex).

EXAMPLE X11

2-Methoxy-2-(2-benzofuranyl)ethanamine

The title compound was prepared from benzofuran-2-aldehyde dimethyl acetal via 1-methoxy-1-(2-benzofuranyl)acetonitrile by an analogous procedure to that described in Example X7.

¹H nmr δ(CDCl₃)
1.4 (2H, exchange with D₂O); 3.1 (2H, d); 3.4 (3H, s); 4.3 (1H, t); 6.65 (1H, s); 7.0–7.6 (4H, complex).

EXAMPLE X12

2-ⁿButoxy-2-(3-chlorophenyl)ethanamine

The title compound was prepared from 3-chlorobenzaldehyde di-ⁿbutyl acetal via 1-ⁿbutoxy-1-(3-chlorophenyl)acetonitrile by an analogous procedure to that described in Example X7.

¹H δ(CDCl₃)
0.7–2.0 (9H, complex), 2.85 (2H, d), 3.2–3.6 (2H, m), 4.25 (1H, t), 7.05–7.5 (4H, complex).

EXAMPLE X13

2-ⁿHexyloxy-2-(3-chlorophenyl)ethanamine

The title compound was prepared from 3-chlorobenzaldehyde di-ⁿhexyl acetal via 1-ⁿhexyloxy-1-(3-chlorophenby an analogous procedure to that described in Example X7.

¹H nmr δ(CDCl₃)
0.6–1.9 (13H, complex), 2.75 (2H, d), 3.2–3.6 (2H, m), 4.2 (1H, t), 7.0–7.4 (4H, complex).

EXAMPLE X14

2-Benzyloxy-2-(3-chlorophenyl)ethanamine

The title compound was prepared from 1-benzyloxy-1-(3-chlorophenyl)acetonitrile by an analogous procedure to that described in Example X2.

¹H nmr δ(CDCl₃)
1.65 (2H, s), 2.8–3.0 (2H, d), 4.2–4.6 (3H, complex), 7.2–7.5 (9H, complex).

EXAMPLE X15

2-Methoxy-3-phenoxypropanamine

2-Methoxy-3-phenoxypropanamine was prepared as an oil from 1-methoxy-2-phenoxypropionitrile by an analogous procedure to that described in Example X2 and used without further purification.

¹H nmr δ(CDCl₃)
1.8–2.0 (2H, brd.m, exchanges with D₂O), 2.8–3.0 (2H, m), 3.4 (3H, s), 3.8–4.0 (3H, m), 6.7–7.4 (5H, m).

EXAMPLE X16

1-Methoxy-2-phenoxypropionitrile

To a solution of 2.45 g of sodium cyanide in 10 ml of dry dimethylformamide was added 9.3 g 1-chloro-1-methoxy-2-phenoxyethane in 10 ml of dimethylformamide. After 48 h at room temperature the solution was poured into water and the organic material extracted with diethyl ether. The organic phase was dried, evaporated and distilled to give the title compound as a pale yellow oil, bp 115°–120° C./1.0 mm.

¹H nmr δ(CDCl₃)
3.5 (3H, s), 4.0–4.5 (3H, m), 6.8–7.4 (5H, m).

EXAMPLE X17

1-Chloro-1-methoxy-2-phenoxyethane

To 36 g of phenoxyacetaldehyde dimethyl acetal was added, dropwise, 40 ml of acetyl chloride and 0.5 ml of thionyl chloride. After 15 h at room temperature the solution was evaporated and the residue distilled under vacuum, 110°–120° C./1 mm, to yield the title compound as a colourless oil.

¹H nmr δ(CDCl₃).
3.50 (3H, s), 4.2 (2H, d), 5.65 (1H, t), 6.7–7.4 (5H, m).

EXAMPLE X18

Phenoxyacetaldehyde dimethyl acetal

A mixture of 31.3 g of phenol, 60.0 g of bromoacetaldehyde dimethyl acetal and 80 g of potassium carbonate was heated at 150° C. in 300 ml of dimethylformamide. After 4.5 hours the reaction mixture was cooled, added to water, and extracted with diethyl ether. Separation, drying and evaporation of the organic phase gave the crude product. Vacuum distillation, bp 88°–98° C./1 mm yielded the title compound as a colourless oil.

EXAMPLE X19

2-Fluorobenzaldehyde dimethylacetal

A mixture of 12.2 g of 2-fluorobenzaldehyde, 15 ml of 2,2-dimethoxypropane and 0.1 g of 4-toluenesulphonic acid was stirred at room temperature. After 24 hours, diethyl ether was added and the resultant solution washed with saturated sodium bicarbonate solution. Drying and evaporation of the organic phase gave the crude acetal. Distillation under vacuum at 90°–95° C./0.08 mm yielded the title compound as a colourless oil.

EXAMPLE X20

1-Methoxy-1-(2-fluorophenyl)acetonitrile

The title compound was prepared from 2-fluorobenzaldehyde dimethylacetal by an analogous procedure to that described in Example X7.

¹H-nmr δ(CDCl₃).
3.42 (3H, s), 5.30 (1H, s), 6.8–7.6 (4H, m).

EXAMPLE X21

2-Methoxy-2-(2-fluorophenyl)ethanamine

The title compound was prepared, as an oil, from 1-methoxy-1-(2-fluorophenyl)acetonitrile by an analogous procedure to that described in Example X2.

$^1$H nmr $\delta$(CDCl$_3$)
2.00 (2H, brd.s, exchanges with D$_2$O) 2.85 (2H, d), 3.26 (3H, s), 4.50 (1H, t), 6.8–7.5 (4H, m).

EXAMPLE X22

2,3-Difluorobenzaldehyde dimethylacetal

The title compound b.p. 58°–62° C. (1 mm Hg) was prepared from 2,3-difluorobenzaldehyde and 2,2-dimethoxypropane by an analogous procedure to that described in Example X19.

EXAMPLE X23

1-Methoxy-1-(2,3-difluorophenyl)acetonitrile

The title compound was prepared from 2,3-difluorobenzaldehyde dimethylacetal by an analogous procedure to that described in Example X7.

$^1$H-nmr $\delta$(CDCl$_3$)
3.44 (3H, s); 5.28 (1H, s); 6.9–7.6 (3H, m).

EXAMPLE X24

2-Methoxy-2-(2,3-difluorophenyl)ethanamine

The title compound was prepared from 2-methoxy-2-(2,3-difluorophenyl)acetonitrile by an analogous procedure to that described in Example X2.

$^1$H nmr $\delta$(CDCl$_3$)
1.5–1.9 (2H, m); 2.80 (2H, d); 3.19 (3H, s); 4.43 (1H, t); 6.6–7.4 (3H, m).

EXAMPLE X25

1-Methoxy-1-(3-methylphenyl)acetonitrile

The title compound was prepared from 3-methylbenzaldehyde dimethylacetal by an analogous procedure to that described in Example X7.

$^1$H-nmr $\delta$(CDCl$_3$)
2.20 (3H, s); 3.36 (3H, s); 5.00 (1H, s); 6.9–7.3 (4H, m).

EXAMPLE X26

2-Methoxy-2-(3-methylphenyl)ethanamine

The title compound was prepared from 1-methoxy-1-(3-methylphenyl)acetonitrile by an analogous procedure to that described in Example X2.

$^1$H-nmr $\delta$(CDCl$_3$)
1.4–1.8 (2H, m); 2.33 (3H, s); 2.82 (2H, d); 3.25 (3H, s); 4.05 (1H, t); 6.8–7.5 (4H, m).

EXAMPLE X27

N-[2-(4-Methylaminocarbonylmethoxyphenyl)-1-(R)-1-methylethyl]-2-(R)-2-methoxy-2-phenylacetamide A solution of 1-hydroxybenzotriazole (0.67 g), dicyclohexylcarbodiimide (1.03 g), 1-(R)-2-[4-methylaminocarbonylmethoxyphenyl]-1-methylethanamine hydrochloride (1.29 g), (R)-α-methoxyphenylacetic acid (0.83 g), triethylamine (0.7 ml) in dimethylformamide (20 ml) was stirred at room temperature for 18 hours and filtered. The filtrate was taken up in ethyl acetate, washed with aqueous sodium carbonate, brine, dilute hydrochloric acid, brine and dried over magnesium sulphate. After filtration and evaporation, the residue was triturated with diethyl ether and filtered to give the title compound, m.p. 130°–2° C., [α]$^{20}$ −29.9° (methanol, c=1) of analytical purity.

$^1$H nmr $\delta$(DMSO-d$_6$)
0.9–1.15 (3H, d), 2.5–2.8 (5H, complex), 3.2 (3H, s), 3.95 (1H, m), 4.35 (2H, s), 4.5 (1H, s), 6.7–7.15 (4H, dd), 7.3 (5H, s), 7.7–8.0 (2H, broad).

DEMONSTRATION OF EFFECTIVENESS OF COMPOUNDS (a) Hypoglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (1 g/Kg body weight) was administered subcutaneously to each mouse. 6 mice were given water as a control. Blood samples were then obtained from each mouse at 30 minute intervals for 120 minutes.

Compounds that produced a significant ($P<0.05$) reduction of blood glucose, compared with control mice given water, at any time interval, were considered active. The area under the blood glucose curve over the 2 hour period after the administration of the glucose was calculated for each compound and compared with the value for control animals.

| Compounds of Example No. | Dose (μmol/Kg) | % Reduction in area under Blood Glucose Curve |
|---|---|---|
| 1 | 0.25 | 47 |
| 2 | 12.5 | 47 |
| 3 | 12.5 | 49 |
| 4 | 1.0 | 54 |
| 5 | 12.5 | 27 |
| 6 | 12.5 | 55 |
| 7 | 2.5 | 32 |
| 8 | 12.5 | 49 |
| 9 | 2.5 | 31 |
| 10 | 1.0 | 24 |
| 11 | 1.0 | 42 |
| 12 | 1.0 | 51 |
| 13 | 2.5 | 21 |
| 15 | 0.5 | 41 |
| 16 | 1.0 | 49 |
| 17 | 2.5 | 25 |
| 18 | 12.5 | 47.5 |
| 19 | 1.0 | 56 |
| 21 | 1.0 | 48 |
| 22 | 25 | 39 |
| 23 | 2.5 | 35 |
| 24 | 12.5 | 51 |
| 25 | 12.5 | 53.5 |
| 26 | 2.5 | 45 |
| 27 | 2.5 | 52 |
| 28 | 2.5 | 55 |
| 29 | 25 | 43 |
| 30 | 12.5 | 26.5 |
| 31 | 12.5 | 29 |
| 32 | 12.5 | 19 |
| 33 | 25 | 52 |
| 34 | 25 | 34 |
| 35 | 12.5 | 10 |
| 36 | 2.5 | 30 |
| 37 | 1.0 | 26 |
| 38 | 25 | 38 |
| 39 | 25 | 15 |
| 40 | 12.5 | 31 |
| 41 | 12.5 | 45 |
| 42 | 5 | 37 |
| 43 | 2.5 | 31 |
| 44 | 7.5 | 34 |
| 45 | 12.5 | 38 |
| 46 | 5 | 20 |

-continued

| Compounds of Example No. | Dose (μmol/Kg) | % Reduction in area under Blood Glucose Curve |
|---|---|---|
| 47 | 12.5 | 41 |
| 48 | 0.5 | 31 |
| 49 | 12.5 | 47 |
| 50 | 2.5 | 41 |
| 51 | 12.5 | 45 |
| 52 | 12.5 | 35 |
| 54 | 25 | 40 |
| 55 | 12.5 | 42 |
| 56 | 12.5 | 40 |
| 57 | 2.5 | 28 |
| 58 | 2.5 | 17 |
| 59 | 25 | 36 |
| 60 | 0.5 | 30.5 |

(b) Effect on Energy Expenditure

The effect of the compounds on the energy expenditure of mice was demonstrated by means of the following procedure:

Female CFLP mice, each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content, following the principles described by J. B. de V. Weir, J. Physiol. (London), 109, 1–9 (1949).

| Compounds of Example No. | Dose mg/kg po | Mean Energy Expenditure | |
|---|---|---|---|
| | | (0–3 h) | (0–21 h) |
| 1 | 21.4 | 151 | 138 |
| 2 | 23.1 | 124 | 113 |
| 3 | 22.1 | 135 | 116 |
| 4 | 8.5 | 152 | 120 |
| 5 | 19.9 | 128 | 117 |
| 6 | 22.5 | 154 | 126 |
| 7 | 23.0 | 143 | 123 |
| 8 | 21.4 | 142 | 111 |
| 9 | 22.4 | 168 | 151 |
| 10 | 20.6 | 135 | 114 |
| 11 | 19.6 | 139 | 118 |
| 12 | 23.6 | 130 | 123 |
| 13 | 20.8 | 145 | 118 |
| 14 | 22.1 | 135 | 103 |
| 15 | 23.6 | 137 | 125 |
| 16 | 22.1 | 140 | 126 |
| 17 | 24.7 | 142 | 130 |
| 18 | 23.2 | 115 | 123 |
| 19 | 22.1 | 143 | 139 |
| 21 | 18.8 | 147 | 120 |
| 22 | 22.1 | 126 | 107 |
| 23 | 23.7 | 163 | 130 |
| 24 | 22.3 | 147 | 128 |
| 25 | 22.8 | 137 | 105 |
| 26 | 22.8 | 122 | 103 |
| 27 | 25.1 | 143 | 115 |
| 28 | 25.1 | 132 | 113 |
| 29 | 23.9 | 144 | 118 |
| 30 | 19.9 | 119 | 115 |
| 31 | 18.5 | 103 | 126 |
| 33 | 21.1 | 148 | 122 |
| 34 | 20.6 | 148 | 116 |
| 35 | 21.0 | 124 | 123 |
| 36 | 21.6 | 131 | 104 |
| 37 | 23.6 | 134 | 106 |
| 39 | 18.5 | 130 | 103 |
| 40 | 20.7 | 128 | 111 |
| 41 | 21.4 | 107 | 116 |
| 42 | 23.5 | 158 | 114 |
| 43 | 24.2 | 144 | 105 |
| 44 | 24.9 | 145 | 101 |
| 46 | 24.2 | 122 | 104 |
| 47 | 21.3 | 130 | 109 |
| 48 | 22.2 | 128 | 131 |
| 49 | 20.6 | 131 | 135 |
| 50 | 24.6 | 142 | 116 |
| 51 | 20.7 | 128 | 108 |
| 52 | 21.1 | 130 | 113 |
| 55 | 20.6 | 150 | 121 |
| 56 | 20.4 | 148 | 108 |
| 57 | 23.8 | 178 | 123 |
| 58 | 22.1 | 131 | 108 |
| 59 | 8.5 | 148 | 111 |
| 60 | 8.6 | 131 | 115 |

(c) Isolated Rat Atria Screen

Sprague-Dawley male rats (300–400 g) are killed and the right and left atria dissected out independently and mounted on a combined tissue holder/electrode. The tissues are then immersed in a glass bath containing Krebs solution maintained at 32° C. The rate of the spontaneously beating right atrium (via an isometric transducer and a ratemeter) and the tension of the electrically paced left atrium (via an isometric transducer) are recorded on an M19 chart recorder.

After an initial stabilization period, the tissues are exposed to a maximal concentration of isoprenaline ($10^{-7}$M). The tissues are then washed several times until rate and tension return to baseline level. A dose-response curve to the test compound is then carried out.

Responses to each concentration of test compound are expressed as a percentage of the maximal responses to isoprenaline. Results are given in the form of (a) intrinsic activity (i.a.) (maximal effect of test compound with respect to isoprenaline maximum, i.e. isoprenaline intrinsic activity=1) and (b) $EC_{50}$ (the molar concentration at which the test compound produces 50% of its own maximum response).

| Compound of Example No. | Rate | | Tension | |
|---|---|---|---|---|
| | $EC_{50}$ (M) | i.a. | $EC_{50}$ (M) | i.a. |
| 1 | — | 0 | $3 \times 10^{-5}$ m | 0.3 |
| 6 | — | 0 | — | 0 |
| 7 | $1.5 \times 10^{-6}$ | 0.06 | $3.6 \times 10^{-5}$ | 0.23 |

(d) ANTI-INFLAMMATORY ACTIVITY

The method used is based on that described by G. Tonelli et al (Endocrinology, 77, 625–634, 1965). An inflammation is induced in the rat ear by the application of 50 μl of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seen compared to non-drug treated control.

| COMPOUND OF EXAMPLE NO. | DOSE mg/rat ear | ACTIVITY |
|---|---|---|
| 1 | 1.00 | Active |
| 29 | 1.00 | Active |

(e) PLATELET AGGREGATION INHIBITION ACTIVITY

Collagen-induced platelet aggregation in human whole blood in vitro.

Collagen added to stirred citrated blood causes platelet aggregation. As the platelets aggregate, the concentration of single platelets falls. Hence the aggregation response can be quantified as a percent fall in single platelet count. Inhibitors of aggregation, such as aspirin and dipyridamole, reduce the response to collagen.

Blood drawn from volunteers who denied taking aspirin within the previous seven days was mixed with 0.1 vol 129 mM trisodium citrate, dispensed into 0.5 ml aliquots and kept at 25° C. Collagen (Hormon-Chemie, Munich) or 154 mM NaCl (control) was added to each aliquot of blood stirred at 1100 rpm in an aggregometer at 37° C. after 3 mins pre-incubation with compound or appropriate solvent. Aggregates were fixed by addition of 0.5 vol 4.5% formaldehyde or 0.05 vol phosphate-buffered glutaraldehyde. Single platelets were counted electronically. Responses, expressed as percent fall in platelet count, were obtained to a range of collagen concentrations. The concentration producing 50% maximal effect (EC50) was estimated from $\log_{10}$ concentration-response curves. Dose-ratios were calculated by dividing the EC50 obtained in the presence of compound under test by the control EC50. Results are summarised in the table.

| COMPOUND | FINAL CONCENTRATION IN WHOLE BLOOD (μM) | DOSE RATIO |
|---|---|---|
| Aspirin | 200 | 2.0 ± 0.1 (3) |
| Dipyridamole | 200 | 3.7 ± 1.1 (4) |
| Example 1 | 300 | 6.9 |
| Example 29 | 100 | 10.8 |

I claim:

1. A compound of the formula (I):

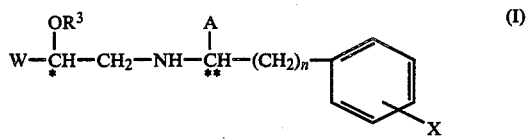

a pharmaceutically acceptable salt, ester, or amide thereof in which W is an optionally substituted phenyl group of the formula:

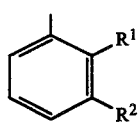

wherein $R^1$ is hydrogen or fluoro; $R^2$ is hydrogen, alkyl of 1 to 6 carbon atoms, halo or trifluoromethyl; or W is phenoxymethyl;

$R^3$ is alkyl of 1 to 12 carbon atoms;

A is hydrogen or methyl;

and X is $-T-Z-CO_2H$ in the para- or meta-position with respect to the $-(CH_2)_n$ group, wherein T is O, S, $-NH$ or $-N-R^7$ in which $R^7$ is alkyl of 1 to 6 carbon atoms, Z is straight chain alkylene of 1 to 10 carbon atoms on branched chain alkylene of up to 10 carbon atoms, said alkylene moieties optionally containing a carbon-carbon double bond and n is 1 or 2.

2. A compound according to claim 1, in which $R^3$ is alkyl of 1 to 6 carbon atoms.

3. A compound according to claim 1 in which $R^2$ is chloro or trifluoromethyl.

4. A compound according to claim 1, in which X is in the para position on the aromatic ring.

5. A compound according to claim 1 which is
N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-carbomethoxymethoxyphenyl)-1-methylethyl]-2-methoxy-2-(3-bromophenyl)ethanamine hydrochloride, or
N-[2-(4-carbomethoxymethoxyphenyl)-1-methylethyl]-2-isopropoxy-2-(3-chlorophenyl)ethanamine hydrochloride.

6. The compound according to claim 1 which is N-[2-(4-carbomethoxymethoxyphenyl)-1-methylethyl]-2-methoxy-2-(3-chlorophenyl)ethanamine hydrochloride.

7. A compound according to claim 1 in which Z is $-CH_2-$.

8. A compound according to claim 1 wherein the compound is:
N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-methylaminocarbonylmethoxyphenyl)-1-methylethyl]-2-methoxy-2-(3-trifluoromethylphenyl)ethanamine hydrochloride,
N-[2-(3-carbomethoxymethoxyphenyl)-1-methylethyl]-2-methoxy-2-(3-chlorophenyl)ethanamine hydrochloride,
N-[2-(4-carbomethoxymethoxyphenyl)-1-methylethyl]-2-methoxy-2-phenylethanamine hydrochloride monohydrate,
N-[2-(4-methylaminocarbonylmethoxyphenyl)-1-methylethyl]-2-methoxy-2-phenylethanamine hydrochloride,
N-[3-(4-carbomethoxymethoxyphenyl)-1-methylpropyl)-2-methoxy-2-(3-chlorophenyl)ethanamine hydrochloride,
N-[2-(4-methylaminocarbonylmethoxyphenyl)-1-methylethyl]-2-methoxy-2-(3-bromophenyl)ethanamine hydrochloride,
N-[2-(4-methylaminocarbonylmethoxyphenyl)-1-methylethyl]-2-ethoxy-2-(3-chlorophenyl)ethanamine hydrochloride, N-[2-(4-dimethylaminocarbonylmethoxyphenyl)-1-methylethyl]-2-methoxy-2-(3-chlorophenyl)ethanamine hydrochloride,
N-[2-(4-aminocarbonylmethoxyphenyl)-1-methylethyl]-2-methoxy-2-(3-chlorophenyl)ethanamine,
N-[3-(4-methylaminocarbonylmethoxyphenyl)-1-methylpropyl]-2-methoxy-2-(3-chlorophenyl)ethanamine hydrochloride,
N-[2-(4-carbomethoxymethoxyphenyl)-1-methylethyl]-2-n-propoxy-2-(3-chlorophenyl)ethanamine hydrochloride,
N-[2-(4-carbomethoxymethoxyphenyl)-1-methylethyl]-2-isopropoxy-2-(3-chlorophenyl)ethanamine hydrochloride,
N-[2-(4-methylaminocarbonylmethoxyphenyl)-1-methylethyl]-2-n-propoxy-2-(3-chlorophenyl)ethanamine dihydrochloride hemihydrate,
N-[2-(4-methylaminocarbonylmethoxyphenyl)-1-methylethyl]-2-isopropoxy-2-(3-chlorophenyl)ethanamine dihydrochloride hemihydrate.
N-[2-(4-carbomethoxymethoxyphenyl)-1-methylethyl]-2-n-butoxy-2-(3-chlorophenyl)ethanamine hydrochloride,
N-[2-(4-methylaminocarbonylmethoxyphenyl)-1-methylethyl]-2-n-butoxy-2-(3-chlorophenyl)ethanamine hydrochloride hemihydrate,
N-[2-(4-carbomethoxymethoxyphenyl)-1-methylethyl]-2-n-hexyloxy-2-(3-chlorophenyl)ethanamine hydrochloride,
N-[2-(4-carbomethoxymethoxyphenyl)-1-methylethyl]-2-benzyloxy-2-(3-chlorophenyl)ethanamine hydrochloride,
N-[2-(4-methylaminocarbonylmethoxyphenyl)ethyl]-2-methoxy-2-(3-chlorophenyl)ethanamine hydrochloride,
N-[2-(4-methylaminocarbonylmethoxyphenyl)-1-methylethyl]-2-methoxy-3-phenoxypropanamine hydrochloride,
N-[2-(4-carbomethoxymethoxyphenyl)-1-methylethyl]-2-methoxy-2-(2,3-difluorophenyl)ethanamine,
N-[2-(4-methylaminocarbonylmethoxyphenyl)-1-methylethyl]-2-methoxy-2-(2,3-difluorophenyl)ethanamine dihydrochloride,
N-[2-(4-methylaminocarbonylmethoxyphenyl)-1-methylethyl]-2-methoxy-2-(2-fluorophenyl)ethanamine hydrochloride,
N-[2-(4-methylaminocarbonylmethoxyphenyl)-1-methylethyl]-2-methoxy-2-(3-methylphenyl)ethanamine hydrochloride,
N-[2-(4-N'-methyl-N'-carbomethoxymethylaminophenyl)-1-methylethyl]-2-methoxy-2-phenylethanamine dihydrochloride, or
N-[2-(4-carbomethoxymethoxyphenyl)-1-methylethyl]-2-methoxy-2-(3-chlorophenyl)ethanamine hydrochloride-(RR,SS) diasteroisomer.

9. A compound according to claim 1 which is:
N-[2-(4-carbomethoxymethoxyphenyl)-1-methylethyl]-2-methoxy-2-(3-chlorophenyl)ethanamine hydrochloride,
N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-methylaminocarbonylmethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-methoxy-2-phenylethanamine hydrochloride monohydrate,
N-[2-(4-carbomethoxymethoxyphenyl)-1-methylethyl]-2-methoxy-2-(3-bromophenyl)ethanamine hydrochloride,
N-[2-(4-methylaminocarbonylmethoxyphenyl)-1-methylethyl]-2-methoxy-2-(3-bromophenyl)ethanamine hydrochloride,
N-[2-(4-methylaminocarbonylmethoxyphenyl)-1-methylethyl]-2-ethoxy-2-(3-chlorophenyl)ethanamine hydrochloride,
N-[2-(4-dimethylaminocarbonylmethoxyphenyl)-1-methylethyl]-2-methoxy-2-(3-chlorophenyl)ethanamine hydrochloride,
N-[2-(4-aminocarbonylmethoxyphenyl)-1-methylethyl]-2-methoxy-2-(3-chlorophenyl)ethanamine,
N-[2-(4-carbomethoxymethoxyphenyl)-1-methylethyl]-2-n-propoxy-2-(3-chlorophenyl)ethanamine hydrochloride,
N-[2-(4-carbomethoxymethoxyphenyl)-1-methylethyl]-2-isopropoxy-2-(3-chlorophenyl)ethanamine hydrochloride,
N-[2-(4-methylaminocarbonylmethoxyphenyl)-1-methylethyl]-2-n-propoxy-2-(3-chlorophenyl)ethanamine dihydrochloride hemihydrate,
N-[2-(4-methylaminocarbonylmethoxyphenyl)-1-methylethyl]-2-isopropoxy-2-(3-chlorophenyl)ethanamine dihydrochloride hemihydrate,
N-[2-(4-carbomethoxymethoxyphenyl)-1-methylethyl]-2-methoxy-2-(2,3-difluorophenyl)ethanamine,
N-[2-(4-methylaminocarbonylmethoxyphenyl)-1-methylethyl]-2-methoxy-2-(2,3-difluorophenyl)ethanamine dihydrochloride,
N-[2-(4-methylaminocarbonylmethoxyphenyl)-1-methylethyl]-2-methoxy-2-(2-fluorophenyl)ethanamine hydrochloride, or
N-[2-(4-carbomethoxymethoxyphenyl)-1-methylethyl]-2-methoxy-2-(3-chlorophenyl)ethanamine hydrochloride-(RR,SS) diasteroisomer.

10. A pharmaceutical composition useful for treating hyperglycaemia and obesity in human and non-human animals which comprises a therapeutically effective amount of a compound of the formula (I):

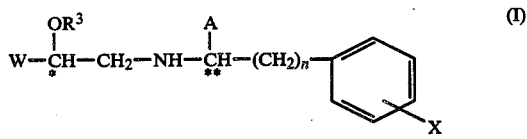

a pharmaceutically acceptable salt thereof, a pharmaceutically acceptable ester thereof, or a pharmaceutically acceptable amide thereof in which W is an optionally substituted phenyl group of the Formula:

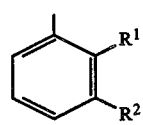

wherein $R^1$ is hydrogen or fluoro; $R^2$ is hydrogen, alkyl of 1 to 6 carbon atoms, halo or trifluoromethyl; or W is phenoxymethyl, $R^3$ is alkyl of 1 to 12 carbon atoms;

A is hydrogen or methyl;

and X is —T—Z—CO$_2$H in the para- or meta-position with respect to the —(CH$_2$)$_n$ group, wherein T is O, S, —NH or —N—$R^7$ in which $R^7$ is alkyl of 1 to 6 carbon atoms, Z is straight chain alkylene of 1 to 10 carbon atoms or branched chain alkylene of up to 10 carbon atoms, said alkylene moieties optionally containing a carbon-carbon double bond and n is 1 or 2, in combination with a pharmaceutically acceptable carrier.

11. A composition according to claim 10, in which $R^3$ is alkyl of 1 to 6 carbon atoms.

12. A composition according to claim 10, in which $R^2$ is chloro or trifluoromethyl.

13. A composition according to claim 10, in which X is in the para position on the aromatic ring.

14. A composition according to claim 10 wherein the compound is

N-[2-(4-carbomethoxymethoxyphenyl)-1-methylethyl]-2-methoxy-2-(3-trifluoromethylphenyl)ethanamine hydrochloride, N-[2-(4-carbomethoxymethoxyphenyl)-1-methylethyl]-2-ethoxy-2-(3-chlorophenyl)ethanamine hydrochloride, N-[2-(4-methylaminocarbonylmethoxyphenyl)-1-methylethyl]-2-methoxy-2-(3-chlorophenyl)ethanamine hydrochloride, N-[2-(4-carbomethoxymethoxyphenyl)-1-methylethyl]-2-methoxy-2-(3-bromophenyl)ethanamine hydrochloride, or N-[2-(4-carbomethoxymethoxyphenyl)-1-methylethyl]-2-isopropoxy-2-(3-chlorophenyl)ethanamine hydrochloride.

15. A composition according to claim 10 wherein the compound is N-[2-(4-carbomethoxymethoxyphenyl)-1-methylethyl]-2-methoxy-2-(3-chlorophenyl)ethanamine hydrochloride.

16. A composition according to claim 10 in which Z is —CH$_2$—.

17. A composition according to claim 10 wherein the compound is:

N-[2-(4-carbomethoxymethoxyphenyl)-1-methylethyl]-2-methoxy-2-(3-trifluoromethylphenyl)ethanamine hydrochloride, N-[2-(4-carbomethoxymethoxyphenyl)-1-methylethyl]-2-ethoxy-2-(3-chlorophenyl)ethanamine hydrochloride, N-[2-(4-methylaminocarbonylmethoxyphenyl)-1-methylethyl]-2-methoxy-2-(3-chlorophenyl)ethanamine hydrochloride, N-[2-(4-methylaminocarbonylmethoxyphenyl)-1-methylethyl]-2-methoxy-2-(3-trifluoromethylphenyl)ethanamine hydrochloride, N-[2-(3-carbomethoxymethoxyphenyl)-1-methylethyl]-2-methoxy-2-(3-chlorophenyl)ethanamine hydrochloride, N-[2-(4-carbomethoxymethoxyphenyl)-1-methylethyl]-2-methoxy-2-phenylethanamine hydrochloride monohydrate, N-[2-(4-methylaminocarbonylmethoxyphenyl)-1-methylethyl]-2-methoxy-2-phenylethanamine hydrochloride, N-[3-(4-carbomethoxymethoxyphenyl)-1-methylpropyl]-2-methoxy-2-(3-chlorophenyl)ethanamine hydrochloride, N-[2-(4-methylaminocarbonylmethoxyphenyl)-1-methylethyl]-2-methoxy-2-(3-bromophenyl)ethanamine hydrochloride, N-[2-(4-methylaminocarbonylmethoxyphenyl)-1-methylethyl]-2-ethoxy-2-(3-chlorophenyl)ethanamine hydrochloride, N-[2-(4-dimethylaminocarbonylmethoxyphenyl)-1-methylethyl]-2-methoxy-2-(3-chlorophenyl)ethanamine hydrochloride, N-[2-(4-aminocarbonylmethoxyphenyl)-1-methylethyl]-2-methoxy-2-(3-chlorophenyl)ethanamine, N-[3-(4-methylaminocarbonylmethoxyphenyl)-1-methylpropyl]-2-methoxy-2-(3-chlorophenyl)ethanamine hydrochloride, N-[2-(4-carbomethoxymethoxyphenyl)-1-methylethyl]-2-n-propoxy-2-(3-chlorophenyl)ethanamine hydrochloride, N-[2-(4-carbomethoxymethoxyphenyl)-1-methylethyl]-2-isopropoxy-2-(3-chlorophenyl)ethanamine hydrochloride, N-[2-(4-methylaminocarbonylmethoxyphenyl)-1-methylethyl]-2-n-propoxy-2-(3-chlorophenyl)ethanamine dihydrochloride hemihydrate, N-[2-(4-methylaminocarbonylmethoxyphenyl)-1-methylethyl]-2-isopropoxy-2-(3-chlorophenyl)ethanamine dihydrochloride hemihydrate, N-[2-(4-carbomethoxymethoxyphenyl)-1-methylethyl]-2-n-butoxy-2-(3-chlorophenyl)ethanamine hydrochloride, N-[2-(4-methylaminocarbonylmethoxyphenyl)-1-methylethyl]-2-n-butoxy-2-(3-chlorophenyl)ethanamine hydrochloride hemihydrate, N-[2-(4-carbomethoxymethoxyphenyl)-1-methylethyl]-2-n-hexyloxy-2-(3-chlorophenyl)ethanamine hydrochloride, N-[2-(4-carbomethoxymethoxyphenyl)-1-methylethyl]-2-benzyloxy-2-(3-chlorophenyl)ethanamine hydrochloride, N-[2-(4-methylaminocarbonylmethoxyphenyl)ethyl]-2-methoxy-2-(3-chlorophenyl)ethanamine hydrochloride, N-[2-(4-methylaminocarbonylmethoxyphenyl)-1-methylethyl]-2-methoxy-3-phenoxypropanamine hydrochloride, N-[2-(4-carbomethoxymethoxyphenyl)-1-methylethyl]-2-methoxy-2-(2,3-difluorophenyl)ethanamine, N-[2-(4-methylaminocarbonylmethoxyphenyl)-1-methylethyl]-2-methoxy-2-(2,3-difluorophenyl)ethanamine dihydrochloride, N-[2-(4-methylaminocarbonylmethoxyphenyl)-1-methylethyl]-2-methoxy-2-(2-fluorophenyl)ethanamine hydrochloride, N-[2-(4-methylaminocarbonylmethoxyphenyl)-1-methylethyl]-2-methoxy-2-(3-methylphenyl)ethanamine hydrochloride, N-[2-(4-N'-methyl-N'-carbomethoxymethylaminophenyl)-1-methylethyl]-2-methoxy-2-phenylethanamine dihydrochloride, or N-[2-(4-carbomethoxymethoxyphenyl)-1-methylethyl]-2-methoxy-2-(3-chlorophenyl)ethanamine hydrochloride-(RR,SS) diasteroisomer.

18. A composition according to claim 10 wherein the compound is:

N-[2-(4-carbomethoxymethoxyphenyl)-1-methylethyl]-2-methoxy-2-(3-chlorophenyl)ethanamine hydrochloride, N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-methylaminocarbonylmethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-methoxy-2-phenylethanamine hydrochloride monohydrate,
N-[2-(4-carbomethoxymethoxyphenyl)-1-methylethyl]-2-methoxy-2-(3-bromophenyl)ethanamine hydrochloride,
N-[2-(4-methylaminocarbonylmethoxyphenyl)-1-methylethyl]-2-methoxy-2-(3-bromophenyl)ethanamine hydrochloride,
N-[2-(4-methylaminocarbonylmethoxyphenyl)-1-methylethyl]-2-ethoxy-2-(3-chlorophenyl)ethanamine hydrochloride,
N-[2-(4-dimethylaminocarbonylmethoxyphenyl)-1-methylethyl]-2-methoxy-2-(3-chlorophenyl)ethanamine hydrochloride,
N-[2-(4-aminocarbonylmethoxyphenyl)-1-methylethyl]-2-methoxy-2-(3-chlorophenyl)ethanamine,
N-[2-(4-carbomethoxymethoxyphenyl)-1-methylethyl]-2-n-propoxy-2-(3-chlorophenyl)ethanamine hydrochloride,
N-[2-(4-carbomethoxymethoxyphenyl)-1-methylethyl]-2-isopropoxy-2-(3-chlorophenyl)ethanamine hydrochloride,
N-[2-(4-methylaminocarbonylmethoxyphenyl)-1-methylethyl]-2-n-propoxy-2-(3-chlorophenyl)ethanamine dihydrochloride hemihydrate,
N-[2-(4-methylaminocarbonylmethoxyphenyl)-1-methylethyl]-2-isopropoxy-2-(3-chlorophenyl)ethanamine dihydrochloride hemihydrate,
N-[2-(4-carbomethoxymethoxyphenyl)-1-methylethyl]-2-methoxy-2-(2,3-difluorophenyl)ethanamine,
N-[2-(4-methylaminocarbonylmethoxyphenyl)-1-methylethyl]-2-methoxy-2-(2,3-difluorophenyl)ethanamine dihydrochloride,
N-[2-(4-methylaminocarbonylmethoxyphenyl)-1-methylethyl]-2-methoxy-2-(2-fluorophenyl)ethanamine hydrochloride, or
N-[2-(4-carbomethoxymethoxyphenyl)-1-methylethyl]-2-methoxy-2-(3-chlorophenyl)ethanamine hydrochloride-(RR,SS) diastereoisomer.

19. A method of treating hyperglycaemia in human and non-human animals which comprises administering to such an animal in need thereof an anti-hyperglycaemically effective amount of a compound of the formula (I):

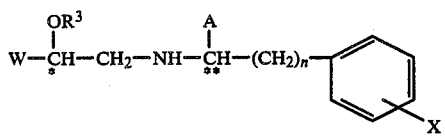

a pharmaceutically acceptable salt thereof, a pharmaceutically acceptable ester thereof, or a pharmaceutically acceptable amide thereof in which W is an optionally substituted phenyl group of the formula:

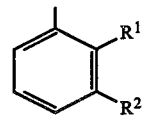

wherein $R^1$ is hydrogen or fluoro; $R^2$ is hydrogen, alkyl of 1 to 6 carbon atoms, halo or trifluoromethyl; or W is phenoxymethyl;
$R^3$ is alkyl of 1 to 12 carbon atoms;
A is hydrogen or methyl;
and X is —T—Z—CO$_2$H in the para- or meta-position with respect to the —(CH$_2$)$_n$ group, wherein T is O, S, —NH or —N—R$^7$ in which R$^7$ is alkyl of 1 to 6 carbon atoms, Z is straight chain alkylene of 1 to 10 carbon atoms or branched chain alkylene of up to 10 carbon atoms, said alkylene moieties optionally containing a carbon-carbon double bond and n is 1 or 2, in combination with a pharmaceutically acceptable carrier.

20. A method according to claim 19, in which $R^3$ is alkyl of 1 to 6 carbon atoms.

21. A method according to claim 19, in which $R^2$ is chloro or trifluoromethyl.

22. A method according to claim 19, in which X is in the para position on the aromatic ring.

23. A method according to claim 19 wherein the compound is
N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-carbomethoxymethoxyphenyl)-1-methylethyl]-2-methoxy-2-(3-bromophenyl)ethanamine hydrochloride, or
N-[2-(4-carbomethoxymethoxyphenyl)-1-methylethyl]-2-isopropoxy-2-(3-chlorophenyl)ethanamine hydrochloride.

24. A method according to claim 19 wherein the compound is N-[2-(4-carbomethoxymethoxyphenyl)-1-methylethyl]-2-methoxy-2-(3-chlorophenyl)ethanamine hydrochloride.

25. A method according to claim 19 wherein Z is —CH$_2$—.

26. A method according to claim 19 wherein the compound is:
N-[2-(4-carbomethoxymethoxyphenyl)-1-methylethyl]-2-methoxy-2-(3-trifluoromethylphenyl)ethanamine hydrochloride,
N-[2-(4-carbomethoxymethoxyphenyl)-1-methylethyl]-2-ethoxy-2-(3-chlorophenyl)ethanamine hydrochloride,
N-[2-(4-methylaminocarbonylmethoxyphenyl)-1-methylethyl]-2-methoxy-2-(3-chlorophenyl)ethanamine hydrochloride,
N-[2-(4-methylaminocarbonylmethoxyphenyl)-1-methylethyl]-2-methoxy-2-(3-trifluoromethylphenyl)ethanamine hydrochloride, N-[2-(3-carbomethoxymethoxyphenyl)-1-methylethyl]-2-methoxy-2-(3-chlorophenyl)ethanamine hydrochloride, N-[2-(4-carbomethoxymethoxyphenyl)-1-methylethyl]-2-methoxy-2-phenylethanamine hydrochloride monohydrate, N-[2-(4-methylaminocarbonylmethoxyphenyl)-1-methylethyl]-2-methoxy-2-phenylethanamine hydrochloride, N-[3-(4-carbomethoxymethoxyphenyl)-1-methylpropyl]-2-methoxy-2-(3-chlorophenyl)ethanamine hydrochloride, N-[2-(4-methylaminocarbonylmethoxyphenyl)-1-methylethyl]-2-methoxy-2-(3-bromophenyl)ethanamine hydrochloride, N-[2-(4-methylaminocarbonylmethoxyphenyl)-1-methylethyl]-2-ethoxy-2-(3-chlorophenyl)ethanamine hydrochloride, N-[2-(4-dimethylaminocarbonylmethoxyphenyl)-1-methylethyl]-2-methoxy-2-(3-chlorophenyl)ethanamine hydrochloride, N-[2-(4-aminocarbonylmethoxyphenyl)-1-methylethyl]-2-methoxy-2-(3-chlorophenyl)ethanamine, N-[3-(4-methylaminocarbonylmethoxyphenyl)-1-methylpropyl]-2-methoxy-2-(3-chlorophenyl)ethanamine hydrochloride, N-[2-(4-carbomethoxymethoxyphenyl)-1-methylethyl]-2-n-propoxy-2-(3-chlorophenyl)ethanamine hydrochloride, N-[2-(4-carbomethoxymethoxyphenyl)-1-methylethyl]-2-isopropoxy-2-(3-chlorophenyl)ethanamine hydrochloride, N-[2-(4-methylaminocarbonylmethoxyphenyl)-1-methylethyl]-2-n-propoxy-2-(3-chlorophenyl)ethanamine dihydrochloride hemihydrate, N-[2-(4-methylaminocarbonylmethoxyphenyl)-1-methylethyl]-2-isopropoxy-2-(3-chlorophenyl)ethanamine dihydrochloride hemihydrate, N-[2-(4-carbomethoxymethoxyphenyl)-1-methylethyl]-2-n-butoxy-2-(3-chlorophenyl)ethanamine hydrochloride, N-[2-(4-methylaminocarbonylmethoxyphenyl)-1-methylethyl]-2-n-butoxy-2-(3-chlorophenyl)ethanamine hydrochloride hemihydrate, N-[2-(4-carbomethoxymethoxyphenyl)-1-methylethyl]-2-n-hexyloxy-2-(3-chlorophenyl)ethanamine hydrochloride, N-[2-(4-carbomethoxymethoxyphenyl)-1-methylethyl]-2-benzyloxy-2-(3-chlorophenyl)ethanamine hydrochloride, N-[2-(4-methylaminocarbonylmethoxyphenyl)ethyl]-2-methoxy-2-(3-chlorophenyl)ethanamine hydrochloride, N-[2-(4-methylaminocarbonylmethoxyphenyl)-1-methylethyl]-2-methoxy-3-phenoxypropanamine hydrochloride, N-[2-(4-carbomethoxymethoxyphenyl)-1-methylethyl]-2-methoxy-2-(2,3-difluorophenyl)ethanamine, N-[2-(4-methylaminocarbonylmethoxyphenyl)-1-methylethyl]-2-methoxy-2-(2,3-difluorophenyl)ethanamine dihydrochloride, N-[2-(4-methylaminocarbonylmethoxyphenyl)-1-methylethyl]-2-methoxy-2-(2-fluorophenyl)ethanamine hydrochloride, N-[2-(4-methylaminocarbonylmethoxyphenyl)-1-methylethyl]-2-methoxy-2-(3-methylphenyl)ethanamine hydrochloride, N-[2-(4-N'-methyl-N'-carbomethoxymethylaminophenyl)-1-methylethyl]-2-methoxy-2-phenylethanamine dihydrochloride, or N-[2-(4-carbomethoxymethoxyphenyl)-1-methylethyl]-2-methoxy-2-(3-chlorophenyl)ethanamine hydrochloride - (RR,SS) diasteroisomer.

27. A method according to claim 19 wherein the compound is:

N-[2-(4-carbomethoxymethoxyphenyl)-1-methylethyl]-2-methoxy-2-(3-chlorophenyl)ethanamine hydrochloride, N-[2-(4-carbomethoxymethoxyphenyl)-1-methylethyl]-2-methoxy-2-(3-trifluoromethylphenyl)ethanamine hydrochloride, N-[2-(4-carbomethoxymethoxyphenyl)-1-methylethyl]-2-ethoxy-2-(3-chlorophenyl)ethanamine hydrochloride, N-[2-(4-methylaminocarbonylmethoxyphenyl)-1-methylethyl]-2-methoxy-2-(3-chlorophenyl)ethanamine hydrochloride, N-[2-(4-methylaminocarbonylmethoxyphenyl)-1-methylethyl]-2-methoxy-2-(3-trifluoromethylphenyl)ethanamine hydrochloride, N-[2-(4-carbomethoxymethoxyphenyl)-1-methylethyl]-2-methoxy-2-phenylethanamine hydrochloride monohydrate, N-[2-(4-carbomethoxymethoxyphenyl)-1-methylethyl]-2-methoxy-2-(3-bromophenyl)ethanamine hydrochloride, N-[2-(4-methylaminocarbonylmethoxyphenyl)-1-methylethyl]-2-methoxy-2-(3-bromophenyl)ethanamine hydrochloride, N-[2-(4-methylaminocarbonylmethoxyphenyl)-1-methylethyl]-2-ethoxy-2-(3-chlorophenyl)ethanamine hydrochloride, N-[2-(4-dimethylaminocarbonylmethoxyphenyl)-1-methylethyl]-2-methoxy-2-(3-chlorophenyl)ethanamine hydrochloride, N-[2-(4-aminocarbonylmethoxyphenyl)-1-methylethyl]-2-methoxy-2-(3-chlorophenyl)ethanamine, N-[2-(4-carbomethoxymethoxyphenyl)-1-methylethyl]-2-n-propoxy-2-(3-chlorophenyl)ethanamine hydrochloride, N-[2-(4-carbomethoxymethoxyphenyl)-1-methylethyl]-2-isopropoxy-2-(3-chlorophenyl)ethanamine hydrochloride, N-[2-(4-methylaminocarbonylmethoxyphenyl)-1-methylethyl]-2-n-propoxy-2-(3-chlorophenyl)ethanamine dihydrochloride hemihydrate, N-[2-(4-methylaminocarbonylmethoxyphenyl)-1-methylethyl]-2-isopropoxy-2-(3-chlorophenyl)ethanamine dihydrochloride hemihydrate, N-[2-(4-carbomethoxymethoxyphenyl)-1-methylethyl]-2-methoxy-2-(2,3-difluorophenyl)ethanamine, N-[2-(4-methylaminocarbonylmethoxyphenyl)-1-methylethyl]-2-methoxy-2-(2,3-difluorophenyl)ethanamine dihydrochloride, N-[2-(4-methylaminocarbonylmethoxyphenyl)-1-methylethyl]-2-methoxy-2-(2-fluorophenyl)ethanamine hydrochloride, or N-[2-(4-carbomethoxymethoxyphenyl)-1-methylethyl]-2-methoxy-2-(3-chlorophenyl)ethanamine hydrochloride - (RR,SS) diasteroisomer.

* * * * *